(12) United States Patent
Steinfeld et al.

(10) Patent No.: US 11,096,651 B2
(45) Date of Patent: Aug. 24, 2021

(54) SYSTEMS AND METHODS FOR MECHANICALLY CALIBRATING A MULTIDETECTOR OF A NUCLEAR MEDICINE IMAGING SYSTEM

(71) Applicant: GE Precision Healthcare LLC, Milwaukee, WI (US)

(72) Inventors: Sergio Steinfeld, Haifa (IL); Moshe Levy, Zichron Yackov (IL); Amir Abecassis, Haifa (IL); Jean-Paul Bouhnik, Zichron Yackov (IL); Ilya Dudarev, Haifa (IL); Omri Warshavski, Misgav (IL); Roee Khen, Haifa (IL); Jonathan Sachs, Haifa (IL); Rani Zananiri, Haifa (IL)

(73) Assignee: GE Precision Healthcare LLC, Milwaukee, WI (US)

( * ) Notice: Subject to any disclaimer, the term of this patent is extended or adjusted under 35 U.S.C. 154(b) by 28 days.

(21) Appl. No.: 16/746,752

(22) Filed: Jan. 17, 2020

(65) Prior Publication Data

US 2021/0219938 A1    Jul. 22, 2021

(51) Int. Cl.
| | |
|---|---|
| *A61B 6/00* | (2006.01) |
| *G01T 1/161* | (2006.01) |
| *G01T 7/00* | (2006.01) |
| *A61B 5/055* | (2006.01) |
| *G01T 1/29* | (2006.01) |

(52) U.S. Cl.
CPC ............ *A61B 6/585* (2013.01); *A61B 5/055* (2013.01); *A61B 6/584* (2013.01); *G01T 1/161* (2013.01); *G01T 1/2914* (2013.01); *G01T 7/005* (2013.01)

(58) Field of Classification Search
None
See application file for complete search history.

(56) References Cited

U.S. PATENT DOCUMENTS

| | | | |
|---|---|---|---|
| 10,702,238 B2* | 7/2020 | Yang | A61B 6/589 |
| 2011/0309252 A1* | 12/2011 | Moriyasu | A61B 6/037 250/362 |
| 2015/0094574 A1 | 4/2015 | Bouhnik et al. | |

* cited by examiner

*Primary Examiner* — Hoon K Song
(74) *Attorney, Agent, or Firm* — McCoy Russell LLP

(57) ABSTRACT

Methods and systems are provided for calibrating a nuclear medicine imaging system having more than 5 detector heads. In one embodiment, a method includes obtaining residual center of gravity determinations corresponding to each of a plurality of detector units based on point source projections acquired over a series of detector unit rotational steps, obtaining center of gravity determinations for each of the plurality of detector units based on point source projections acquired over a series of detector unit sweep angles, obtaining a fit of the center of gravity determinations for each of the plurality of detector units, and determining a sweep offset for each of the plurality of detector units based on the residual center of gravity determinations and the fit of the center of gravity determinations for each of the plurality of detector units. In this way, a sweep axis zero degree position for each of the plurality of detector units is determined.

20 Claims, 23 Drawing Sheets

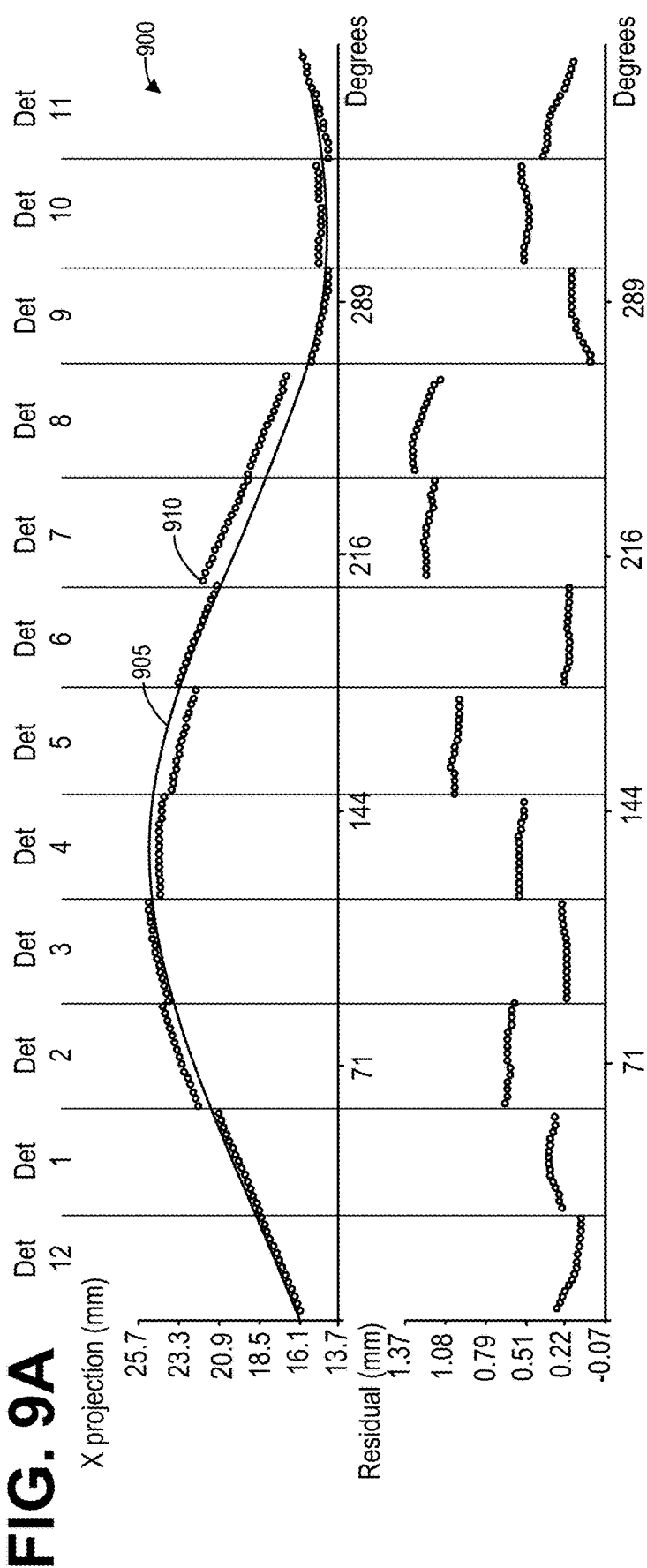

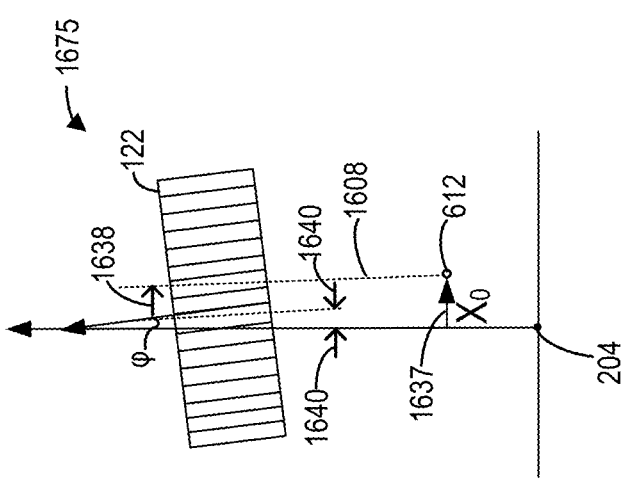
FIG. 16A
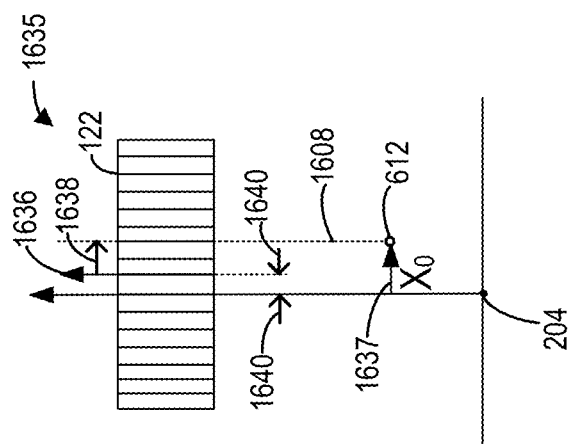
FIG. 16B  FIG. 16C
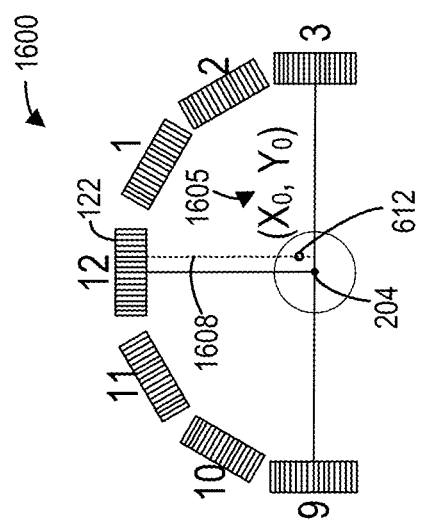

SYSTEMS AND METHODS FOR MECHANICALLY CALIBRATING A MULTIDETECTOR OF A NUCLEAR MEDICINE IMAGING SYSTEM

FIELD

Embodiments of the subject matter disclosed herein relate to medical imaging systems, and more particularly, to calibrating a nuclear medicine (NM) imaging system.

BACKGROUND

In nuclear medicine imaging, systems with multiple detectors or detector heads may be used to image a subject. For example, the detectors may be moved radially to be positioned adjacent to the subject to acquire nuclear medicine imaging data (e.g., radioactivity), which is used to generate a three-dimensional (3D) image of the subject. In a specific example, Single Photon Emission Computed Tomography (SPECT) systems may have moving detector heads, such as gamma cameras, positioned to focus on a region of interest. One or more of the gamma cameras may be moved (for example, rotated) to different angular positions to acquire image data. The acquired image data may then be used to generate 3D images.

BRIEF DESCRIPTION

In one embodiment, a method for calibrating a nuclear medicine imaging system comprises: in a first step, acquiring first point source projections of a point source at each of a plurality of detector units over a predetermined number of detector unit rotational steps, converting the first point source projections to first center of gravity measurements for each of the plurality of detector units with respect to an x-axis of each of the plurality of detector units, fitting the first center of gravity measurements to obtain a first fit, and obtaining a residual center of gravity determination for each of the plurality of detector units based on a difference between the first center of gravity measurements and the first fit corresponding to each of the plurality of detector units; in a second step, acquiring second point source projections for each of the plurality of detector units at a predetermined number of sweep angles, converting the second point source projections to second center of gravity measurements for each of the plurality of detector units, fitting the second center of gravity measurements to obtain a second fit for each of the plurality of detector units; and determining a sweep offset for each of the plurality of detector units based on the residual center of gravity determination for each detector unit and the second fit obtained for each detector unit.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 9A depicts a graph illustrating sweep offsets calculated for a plurality of detector units in accordance with an embodiment;

FIG. 9B depicts residuals associated with the sweep offsets of FIG. 9A in accordance with an embodiment;

FIGS. 16A-16C schematically illustrate how x-shift offset measurements are obtained via the method of FIG. 15, according to an embodiment;

DETAILED DESCRIPTION

The following description relates to various embodiments of nuclear medicine (NM) imaging systems. Specifically, in order for acquired image data to be reconstructed into an accurate image, relevant components of the imaging system may have to be calibrated to a high degree of accuracy. If the system components are not properly calibrated, artifacts may be introduced into reconstructed images, which may hinder the ability of a professional to accurately diagnose a patient.

The process of calibrating such a complex system can be a challenging, time-consuming and expensive process. As one example, the calibration process may be carried out for particular nuclear medicine imaging systems with a mechanically accurate (and expensive) jig. However, reliance on a jig may be a cumbersome and inefficient process, particularly for a nuclear medicine imaging system with a plurality of detector heads that are rotationally mounted to a gantry that surrounds a patient table. For example, in single photon imaging systems, such as planar or SPECT imaging systems, collimators may be placed in front of a scintillation crystal or solid state detector to image the field of view (FOV) onto the detectors. The collimators allow gamma rays aligned with the holes of the collimators to pass through to the detector. These detectors need to be calibrated, including during manufacture and periodically after installation, to ensure proper imaging operation. For example, the detectors may be calibrated to provide a uniform energy and sensitivity response across the detector units or output channels. In some examples, calibration of such collimated detectors may be performed on the detectors having the collimators removed and using a jig or a guide. Yet due to the detectors having to be disassembled, such an approach is time-consuming and difficult.

Thus, discussed herein systems and methods are provided for calibrating a NM imaging system such that a sweep offset, a z-shift, an x-shift, and a yaw angle are determined for a plurality of individual detector units. Based on such determinations, the NM imaging system may be properly calibrated and reconstructed images of a desired quality may be obtained.

Figure 1:
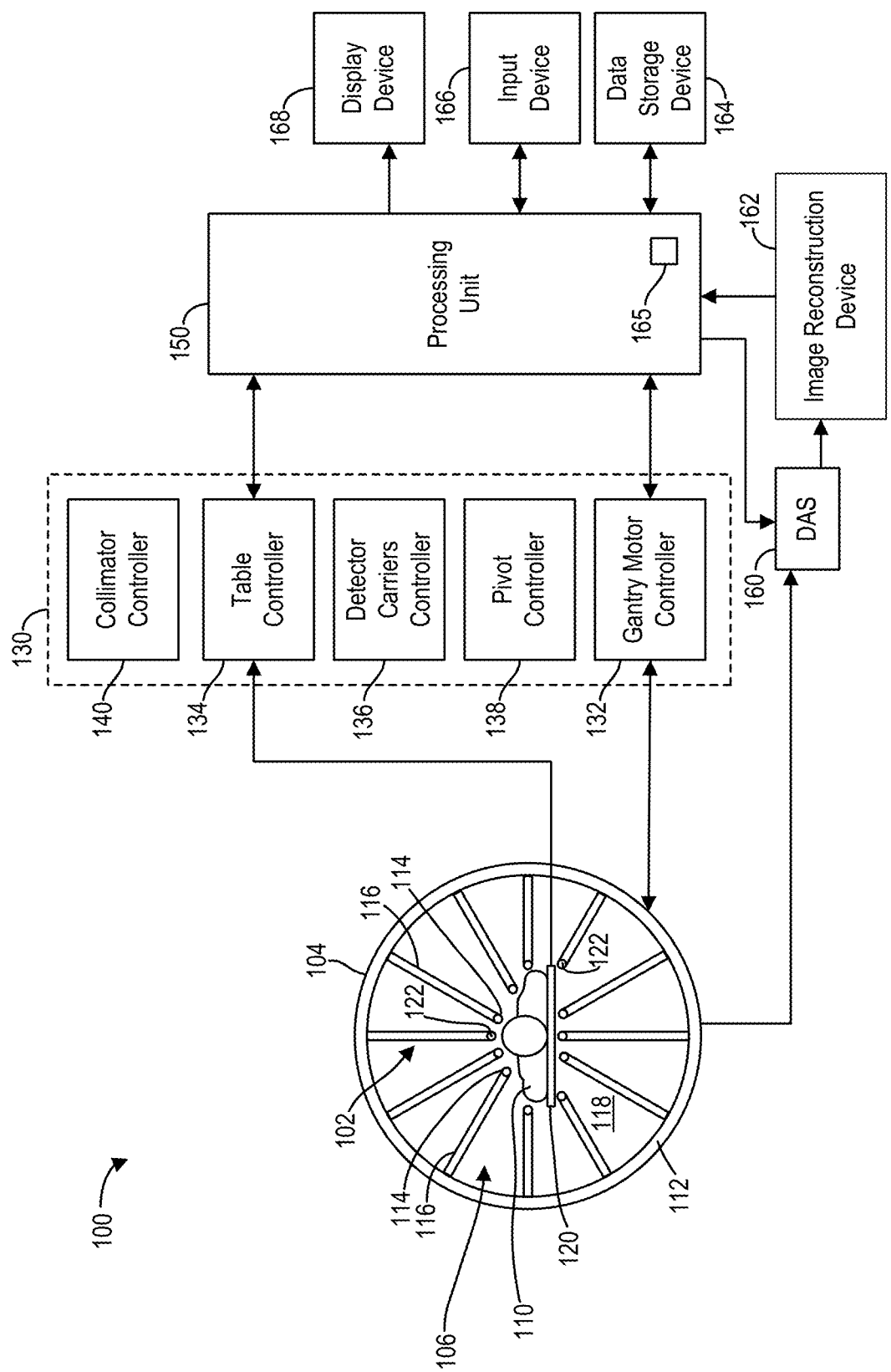
FIG. 1 is a schematic block diagram of a nuclear imaging (NM) imaging system in accordance with an embodiment.
Figure 3B:
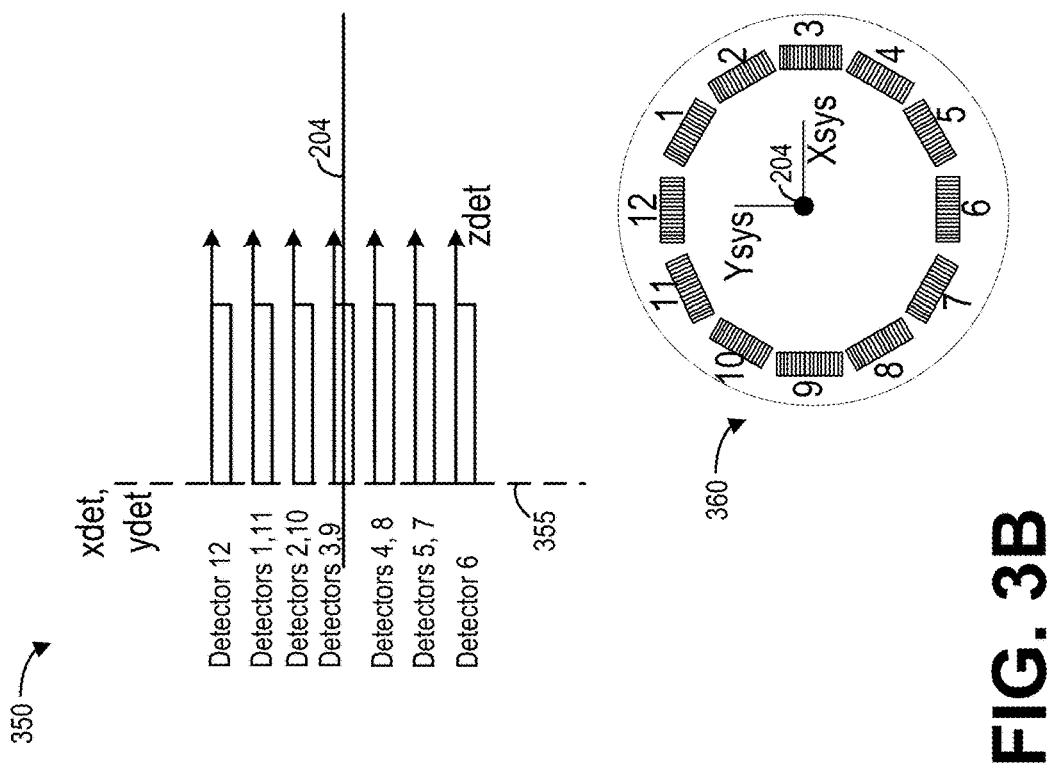
FIG. 3B shows a plurality of detector units when viewed along the x axis of the NM imaging system.
Figure 4:
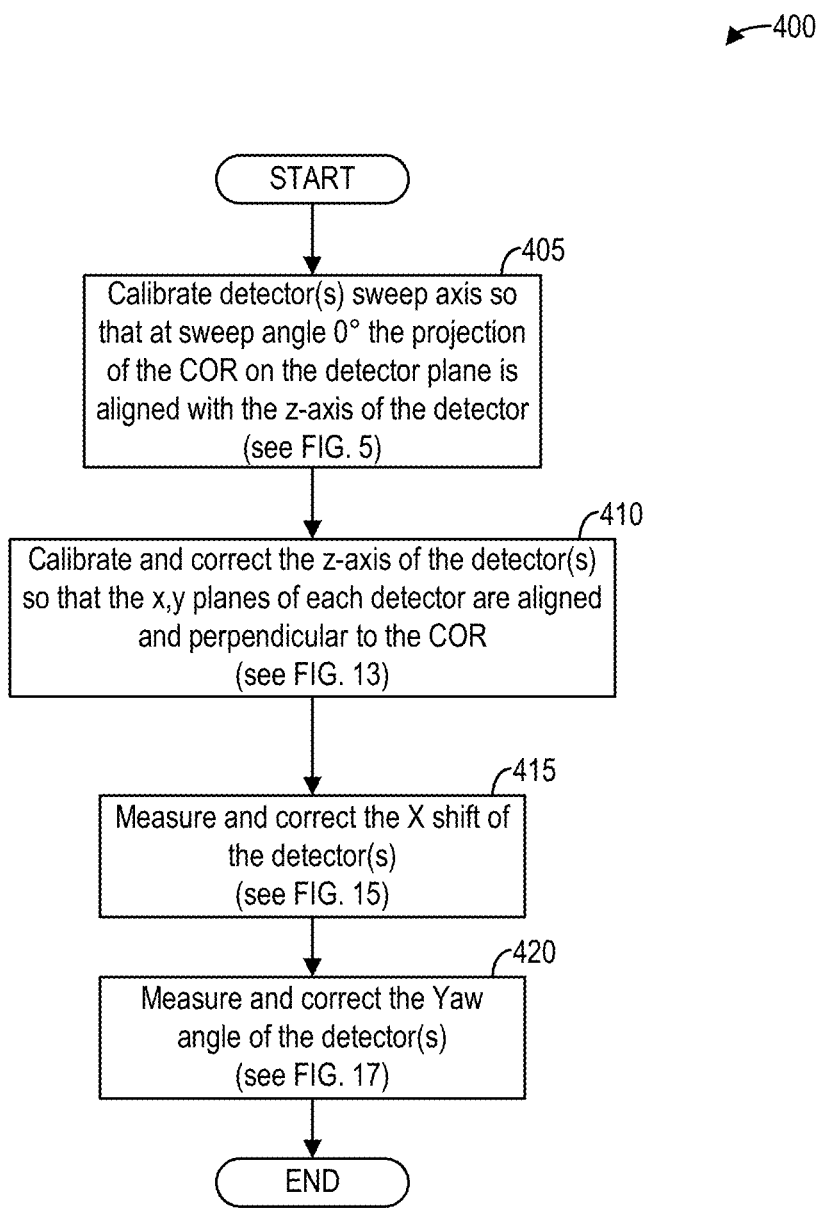
FIG. 4 shows a high-level flow chart illustrating an example methodology for calibrating the NM imaging system in accordance with an embodiment.
Figure 5:
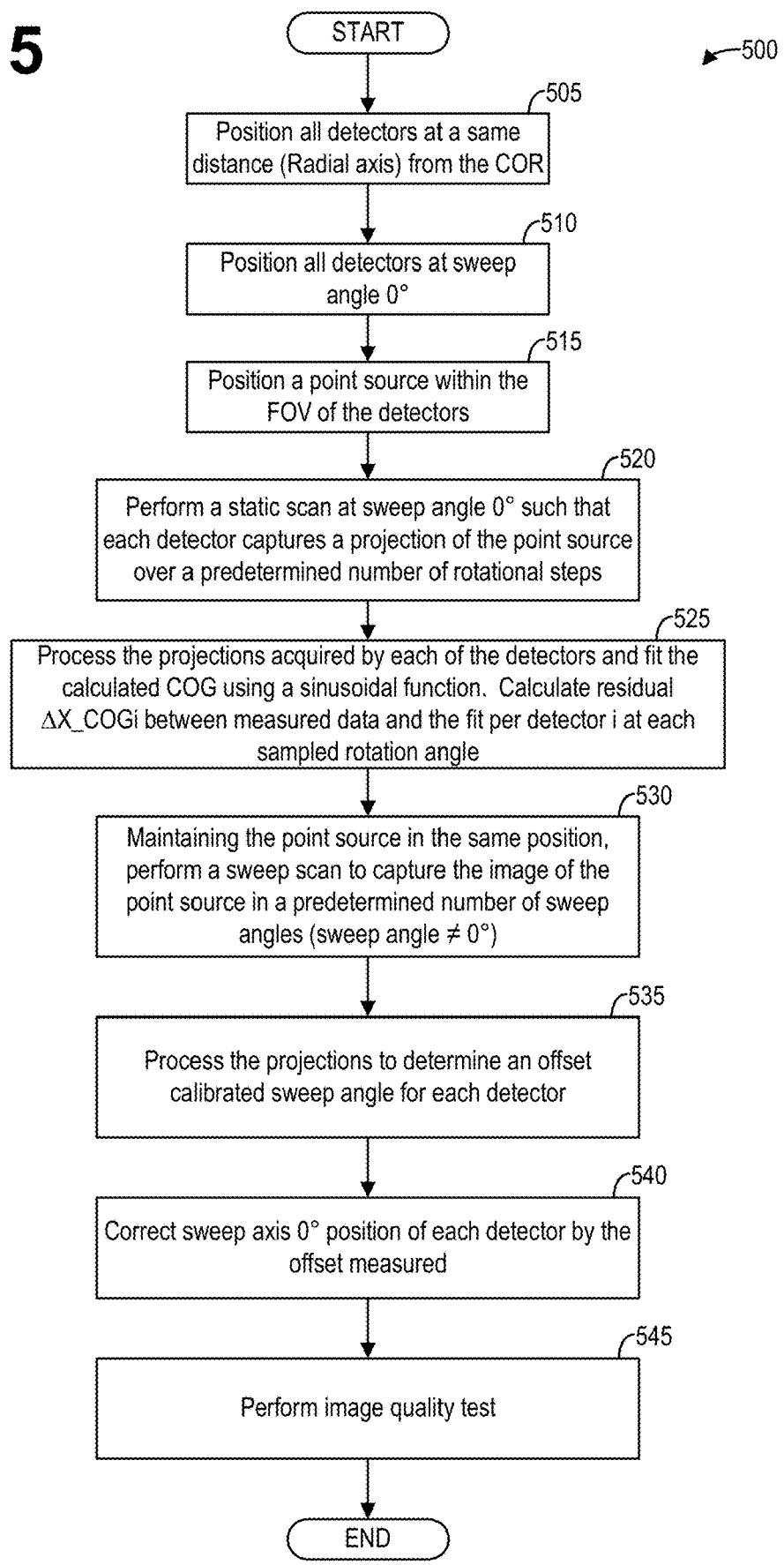
FIG. 5 shows a high-level flow chart illustrating an example methodology for calibrating a sweep axis of a plurality of individual detector units in accordance with an embodiment.
Figure 11:
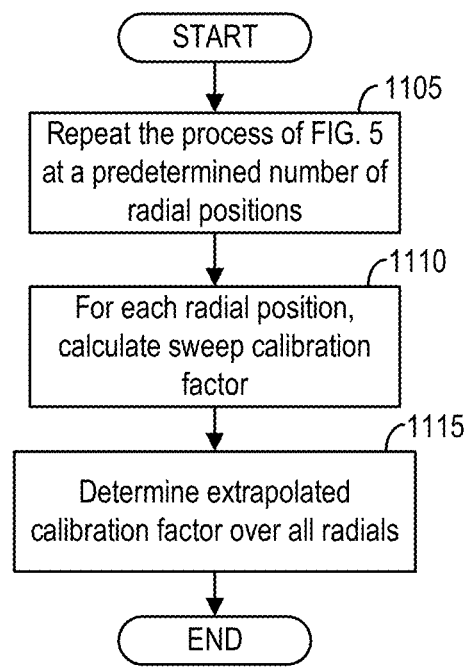
FIG. 11 shows a high-level flow chart illustrating an example methodology for conducting the method of FIG. 5 at different detector unit radial positions in accordance with an embodiment.
Figure 12:
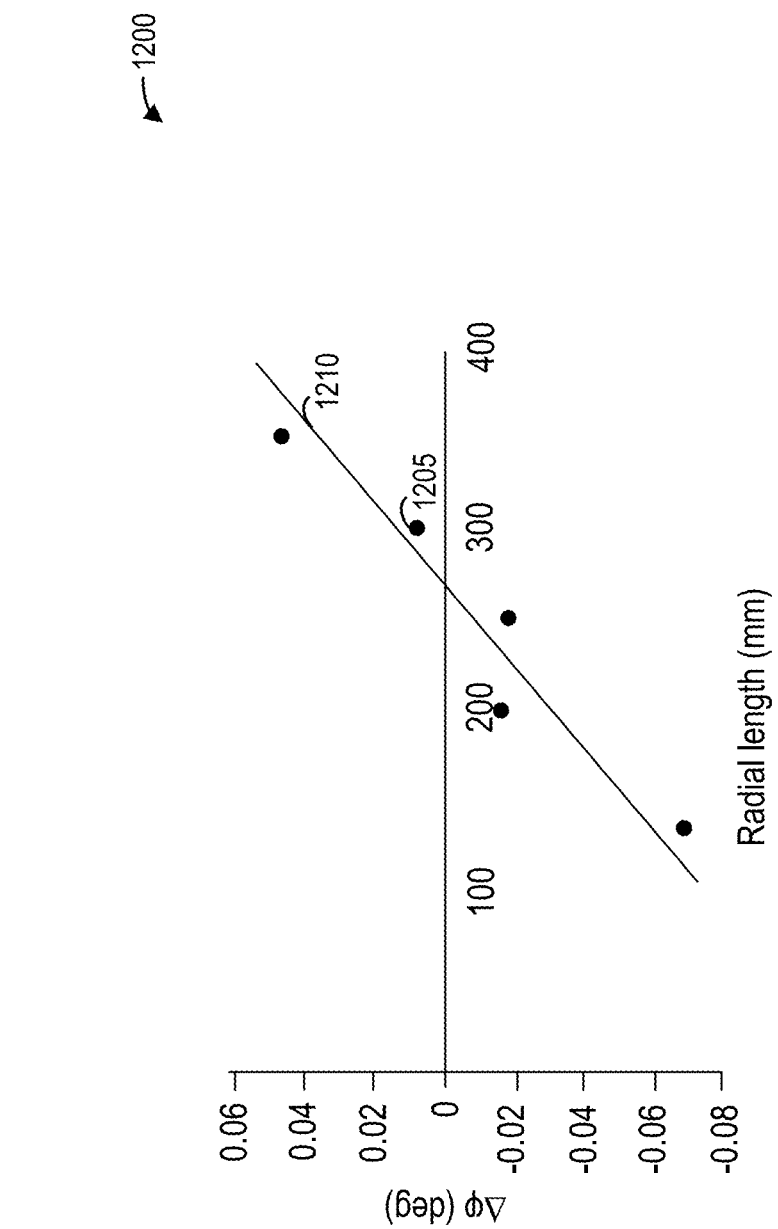
FIG. 12 shows an example graph depicting the type of data obtained via the method of FIG. 11 in accordance with an embodiment.
Figure 13:
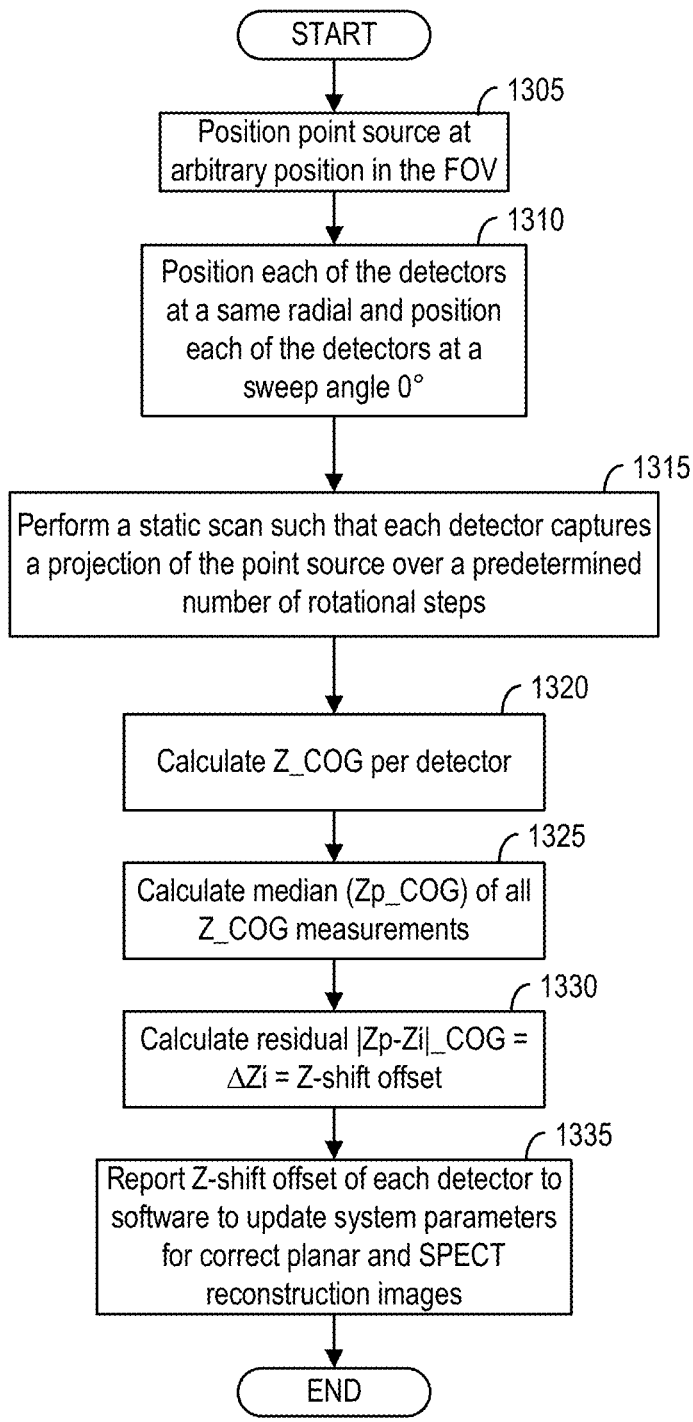
FIG. 13 shows a high-level example method for determining a z-shift offset for each of a plurality of individual detector units, in accordance with an embodiment.
Figure 14B:
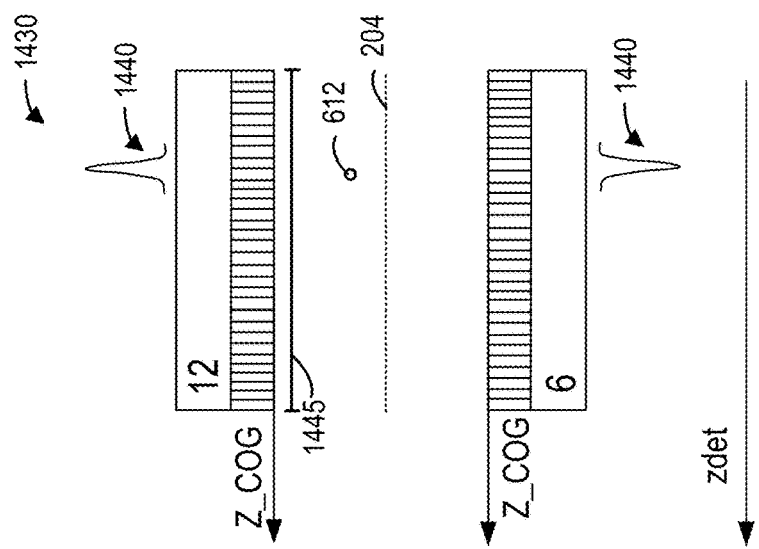
FIGS. 14A-14C schematically illustrate how center of gravity determinations made with respect to the z-axis of individual detector units are used to obtain the z-shift offset for individual detector units via the method of FIG. 13, in accordance with an embodiment.
Figure 14A:
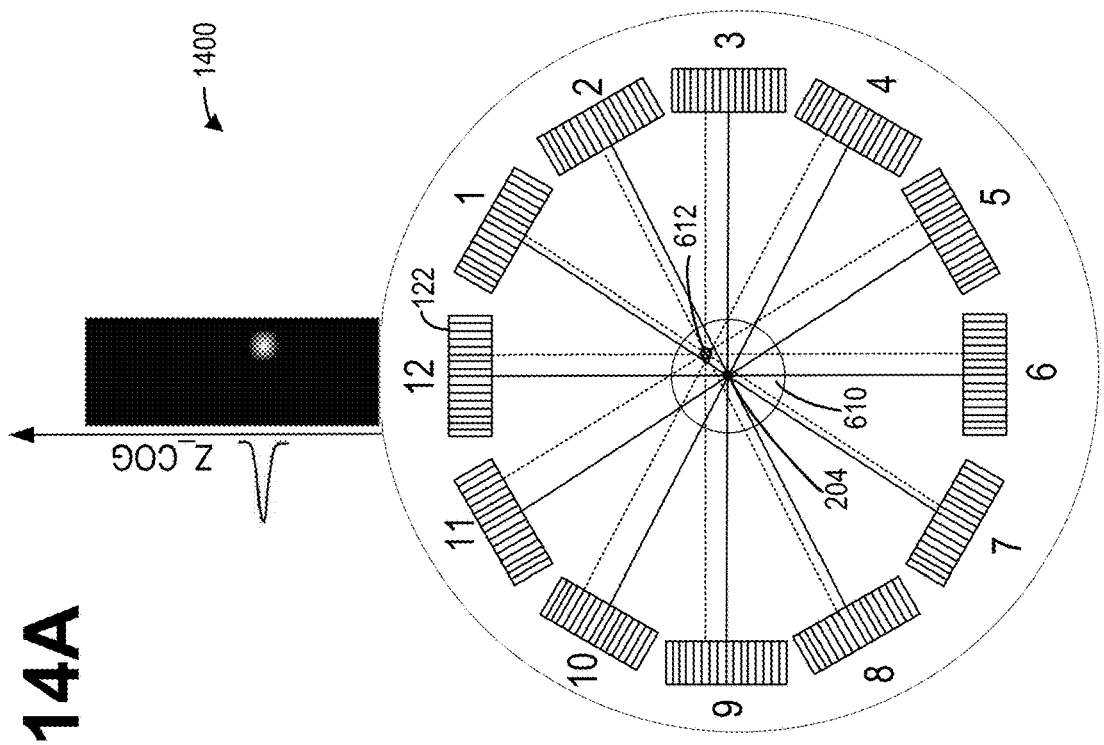
Figure 14C:
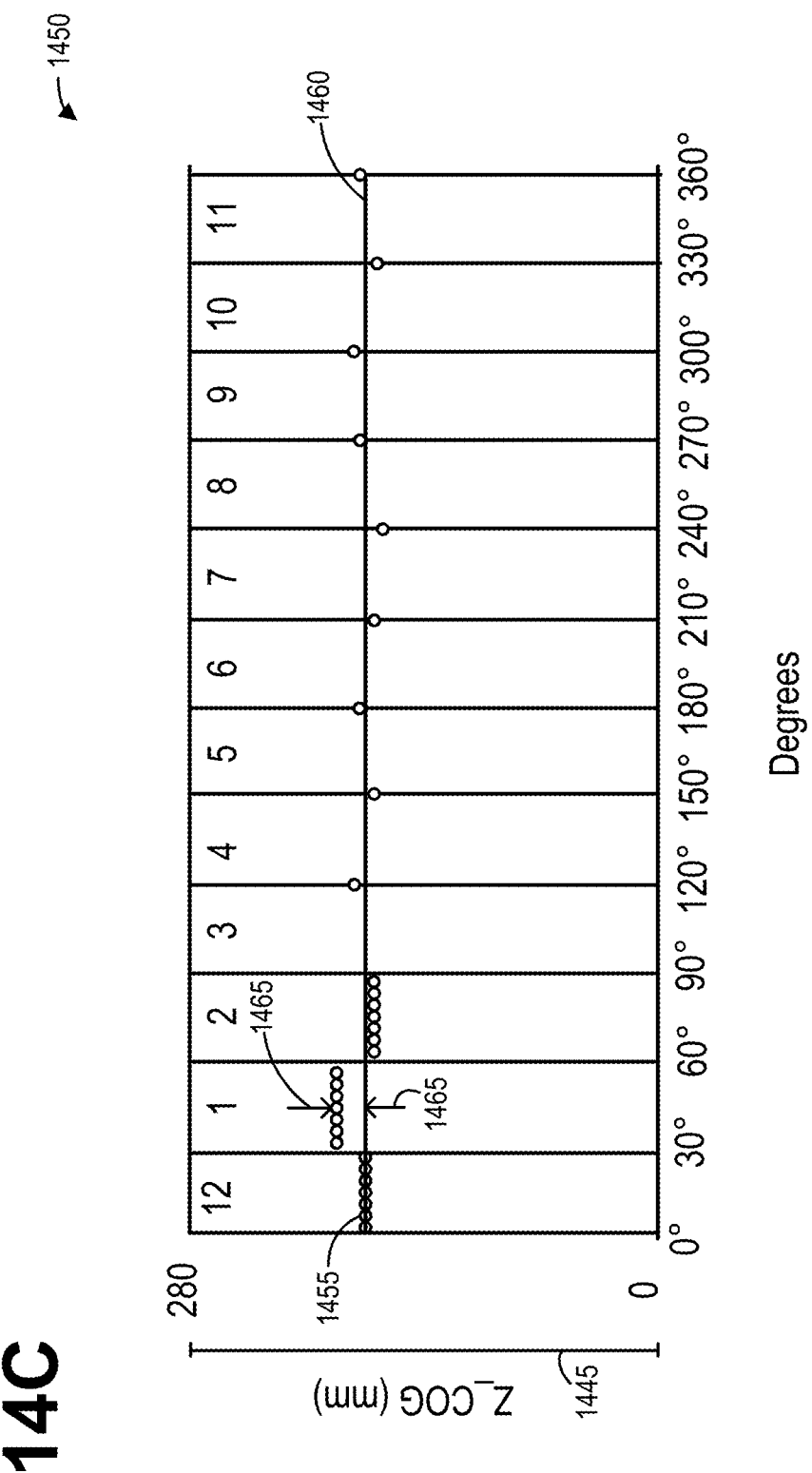
Figure 15:
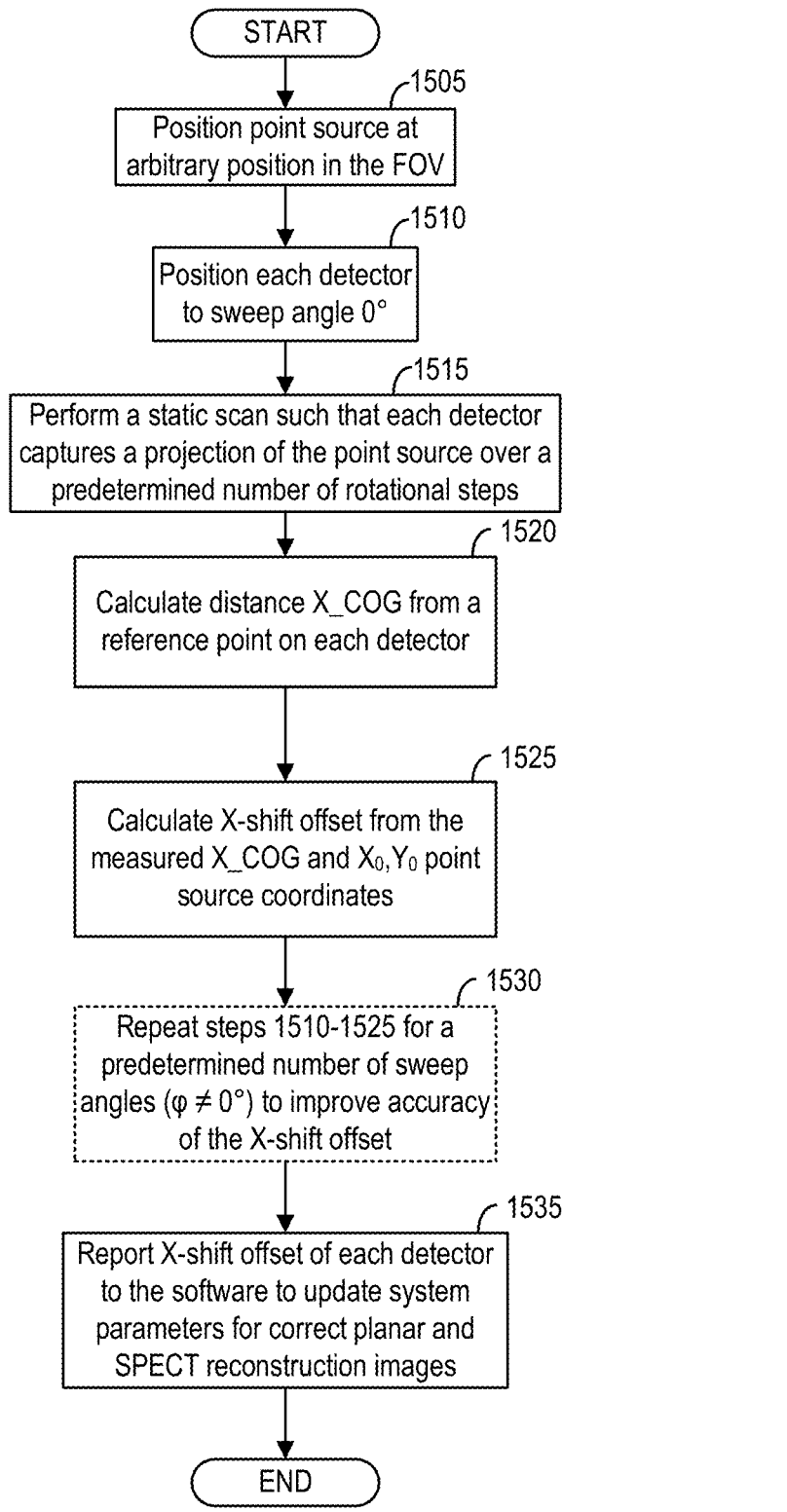
FIG. 15 shows a high-level example method for determining an x-shift offset for each of a plurality of individual detector units, in accordance with an embodiment.
Figure 17:
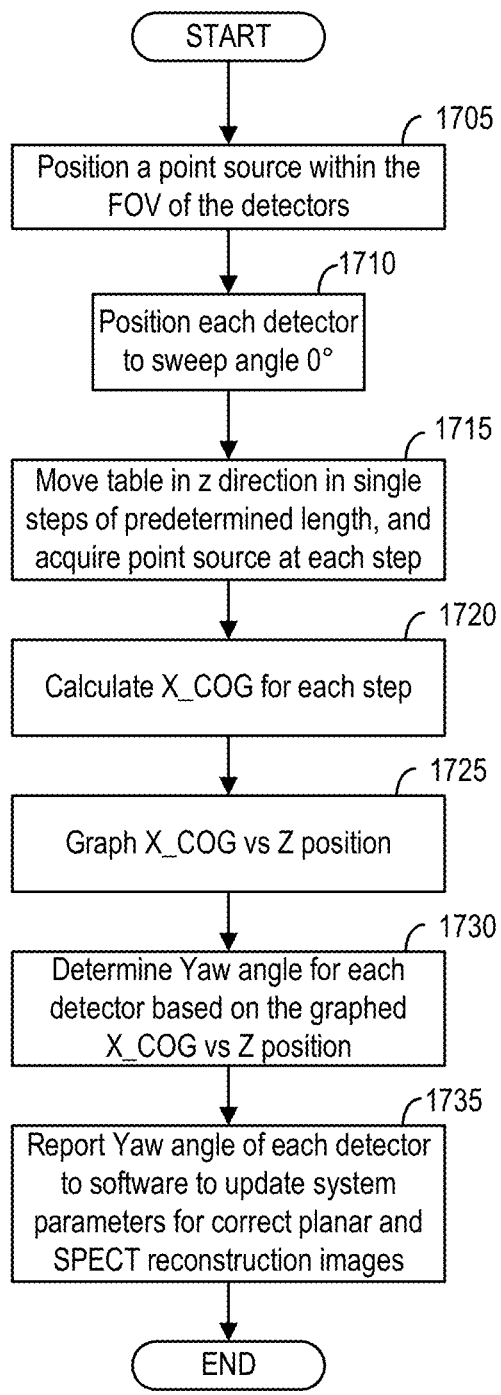
FIG. 17 shows a high-level example method for determining a yaw angle of individual detector units, in accordance with an embodiment.
Figure 18:
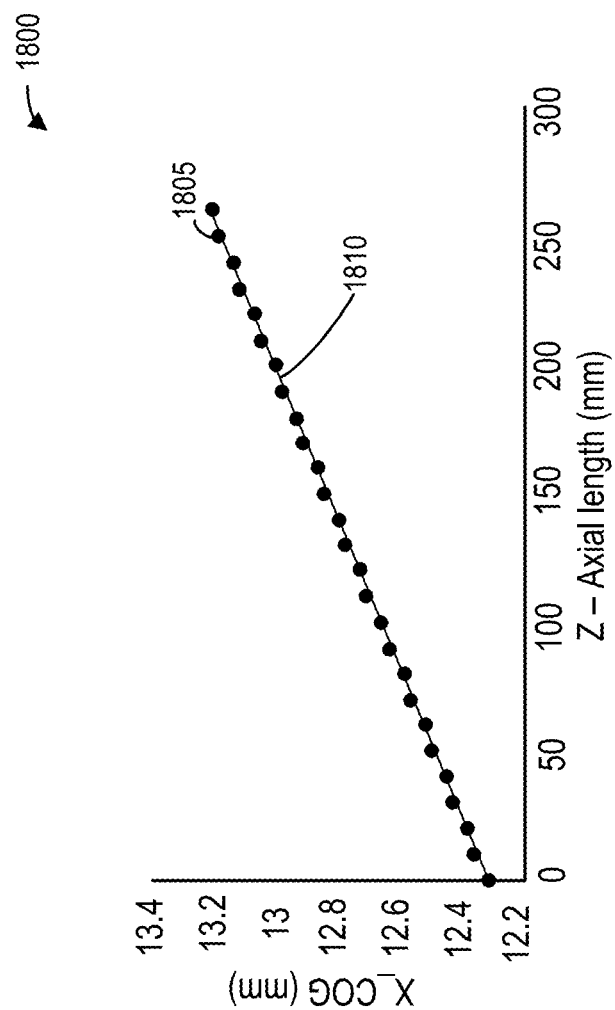
FIG. 18 shows an example graph depicting the type of data obtained via the method of FIG. 17 for use in determining the yaw angle of individual detector units, in accordance with an embodiment.
Figure 19B:
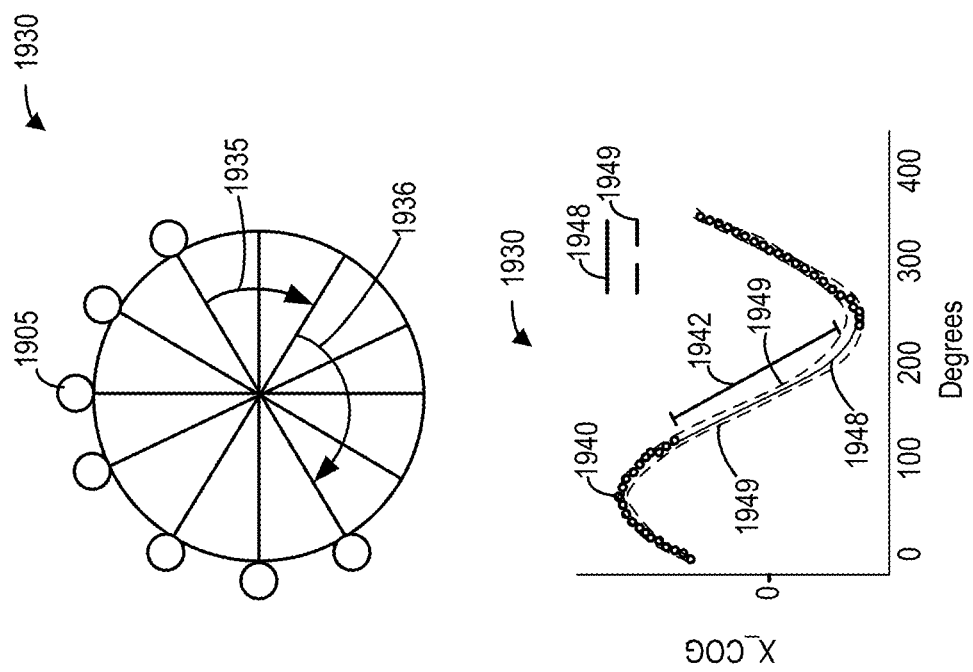
FIGS. 19A-19B show portions of NM imaging systems that include less than 12 individual detector units, in accordance with an embodiment.
Figure 19A:
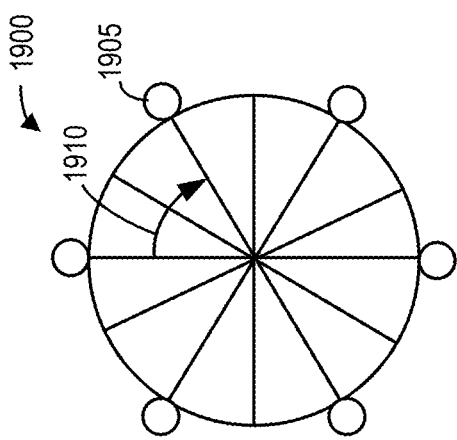
Figure 20:
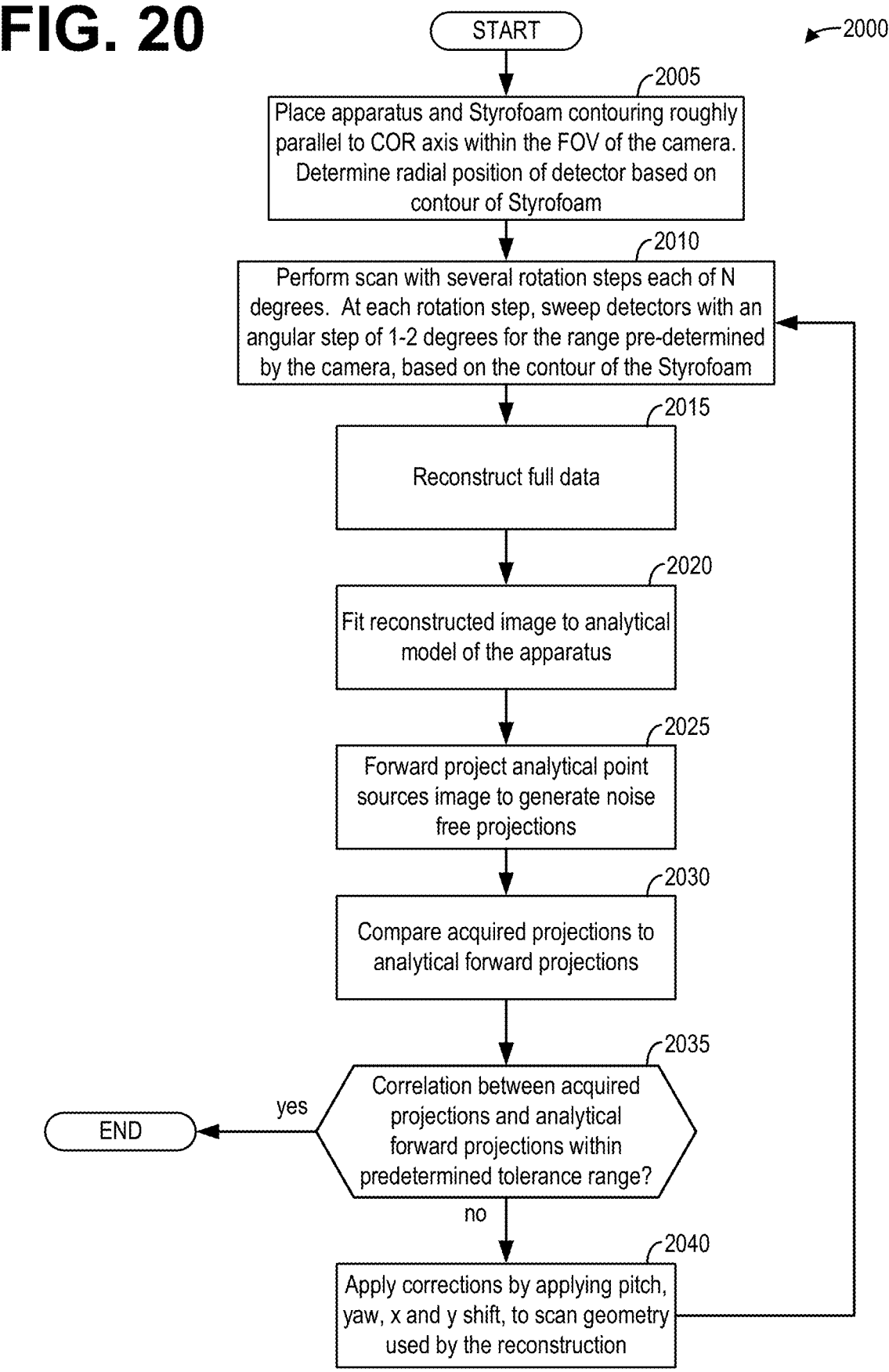
FIG. 20 depicts a high-level example method for a geometric calibration procedure for the NM system of FIG. 1 that uses a linear array of equidistant radioactive point sources.
Figure 21:
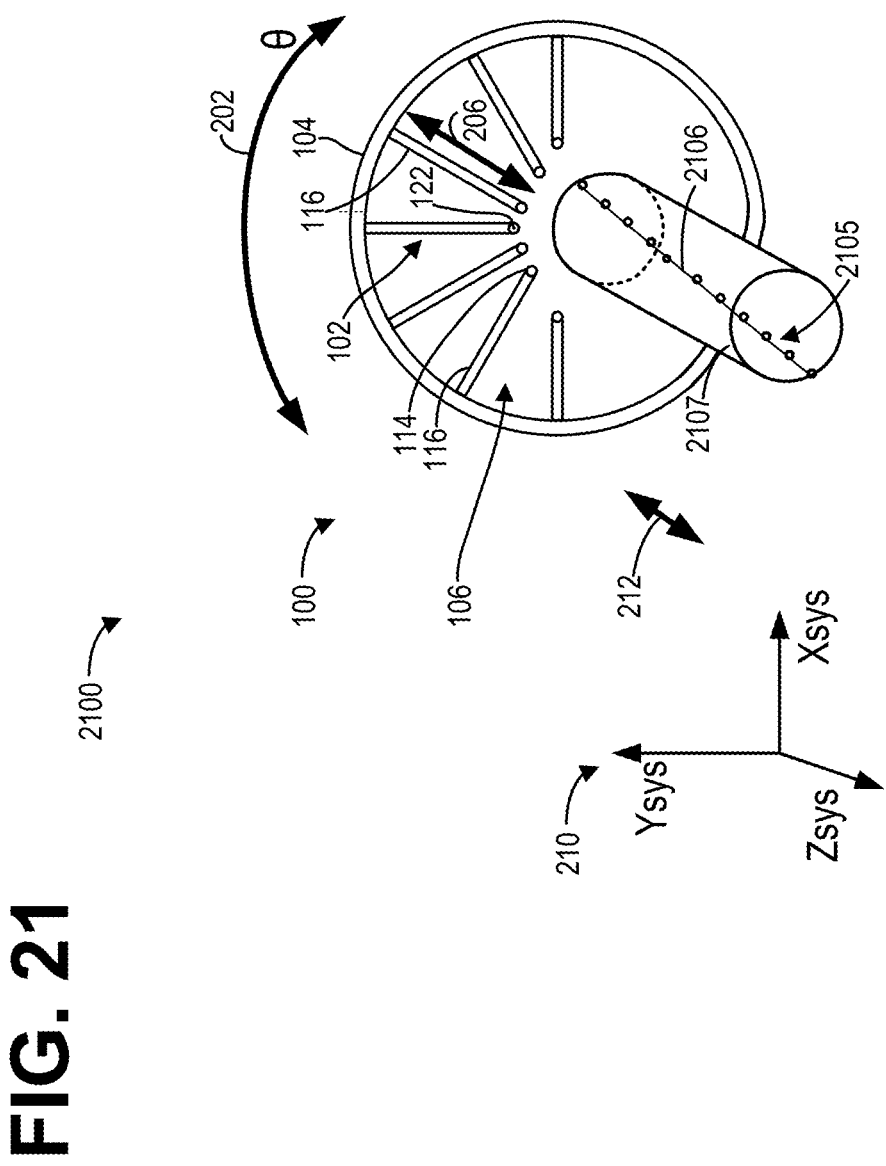
FIG. 21 depicts an illustration that includes the linear array of equidistant radioactive point sources of FIG. 20.

Accordingly, an imaging system, such as the imaging system of FIG. 1, may include systems for controlling the movement of a plurality of imaging detectors in order to position the imaging detectors for acquisition of image data. FIGS. 2A-3B depict various viewpoints of aspects of the NM imaging system of FIG. 1, for defining relevant axes corresponding to the NM imaging system and individual detector units to provide an understanding of the sweep offset, z-shift, x-shift and yaw angle. An overall methodology for calibrating the NM imaging system in terms of the sweep offset, z-shift, x-shift and yaw angle for individual detector units is depicted at FIG. 4. FIG. 5 depicts a sub-method of FIG. 4, and is used to determine the sweep offset for individual detector units. FIGS. 6A-10 include illustrations relevant to understanding the process flow of the method of FIG. 5. In some examples, the sweep offset as discussed with regard to FIG. 5 may be determined at a number of different radial positions for the detector units, via the method of FIG. 11. FIG. 12 depicts an example of the type of data obtained via the method of FIG. 11, which can be used to determine an extrapolated calibration factor corresponding to sweep angle offset for individual detector units. FIG. 13 depicts a sub-method of FIG. 4, and is used to determine the z-shift for individual detector units. FIGS. 14A-14C include illustrations relevant to understanding the process flow of the method of FIG. 13. FIG. 15 depicts another sub-method of FIG. 4, and is used to determine the x-shift for individual detector units. FIGS. 16A-16C include illustrations relevant to understanding the process flow of the method of FIG. 15. FIG. 17 depicts another sub-method of FIG. 4, and is used to determine the yaw angle of individual detector units. FIG. 18 depicts an example graph of data acquired via the method of FIG. 17, which is used to determine the yaw angle for individual detector units. FIGS. 19A-19B show example NM imaging systems with varying numbers of individual detector units. FIG. 20 depicts a high level example method for a geometric calibration procedure for the NM systems discussed herein, that relies on a linear array of equidistant radioactive point sources and a Styrofoam object. FIG. 21 depicts an illustration that includes the linear array of equidistant radioactive point sources and the Styrofoam object, to provide reference for the methodology of FIG. 20.

FIG. 1 is a schematic illustration of a NM imaging system 100 having a plurality of imaging detectors mounted on a gantry. The imaging detectors may be configured to rotate around a fixed pivot. The movement of the imaging detectors is controlled to reduce the likelihood or avoid collision among the moving imaging detectors and/or reduce the likelihood of one imaging detector obstructing the field of view of another imaging detector. For example, the NM imaging system in some embodiments provides coordinated swinging or rotating motion of a plurality of imaging detectors or detector heads.

In particular, a plurality of imaging detectors 102 are mounted to a gantry rotor 104 and/or a patient support structure (not shown) (e.g., under a patient table 120), which may define a table support for a patient table 120. In the illustrated embodiment, the imaging detectors 102 are configured as a detector array 106 positioned around the subject 110 (e.g., a patient), as viewed in FIG. 1. The detector array 106 may be coupled directly to the gantry rotor 104, or may be coupled via support members 112 thereto, to allow movement of the entire array 106 relative to the gantry rotor 104 (e.g., rotational movement in the clockwise or counterclockwise direction as viewed in FIG. 1). Additionally, each of the imaging detectors 102 includes a detector unit 114, at least some of which are mounted to a movable detector carrier 116 (e.g., a support arm or actuator that may be driven by a motor to cause movement thereof) that extends from the gantry rotor 104. In some embodiments, the detector carriers 116 allow movement of the detector units 114 towards and away from the subject 110, such as linearly. Thus, in the illustrated embodiment the detector array 106 is around the subject 110 and may allow linear movement of the detector units 114, such as towards or away from the patient table 120 in one embodiment. However, other configurations and orientations are possible as described herein, as well as different types of movements (e.g., transverse or perpendicular movement relative to the patient table 120). It should be noted that the movable detector carrier 116 may be any type of support that allows movement of the detector units 114 relative to the support member 112 and/or gantry rotor 104, which in various embodiments allows the detector units 114 to move linearly towards and away from the support member 112, such as radially inward and outwards for positioning adjacent the subject 110. For example, as described herein, the detector units 114 may be controlled to move independently of each other towards or away from the subject 110, as well as capable of rotational, pivoting, or tilting movement in some embodiments.

Each of the imaging detectors 102 in various embodiments is smaller than a conventional whole body or general purpose imaging detector. A conventional imaging detector may be large enough to image most or all of a width of a patient's body at one time and may have a diameter of approximately 50 cm or more. In contrast, each of the imaging detectors 102 may include one or more detector units 114 coupled to a respective detector carrier 116 and having dimensions of 4 cm to 20 cm and may be formed of Cadmium Zinc Telluride (CZT) tiles or modules. For example, each of the detector units 114 may be 8×8 cm in size and be composed of a plurality of CZT pixelated modules (not shown). For example, each module may be 4×4 cm in size and have 16×16=256 pixels. In some embodiments, each detector unit 114 includes a plurality of modules, such as an array of 1×7 modules. However, different configurations and array sizes are contemplated including, for example, detector units 114 having multiple rows of modules.

It should be understood that the imaging detectors may be different sizes and/or shapes with respect to each other, such as square, rectangular, circular, or another shape. An actual field of view (FOV) of each of the imaging detectors 102 may be directly proportional to the size and shape of the respective imaging detector.

The gantry rotor 104 may be formed with an aperture 118 (e.g., opening or bore) therethrough as illustrated. The patient table 120 is configured with a support mechanism, such as the patient support structure, to support and carry the subject 110 in one or more of a plurality of viewing positions within the aperture 118 and relative to the imaging detectors 102. Alternatively, the gantry rotor 104 may comprise a plurality of gantry segments (not shown), each of which may independently move a support member 112 or one or more of the imaging detectors 102.

The gantry rotor 104 may also be configured in other shapes, such as a "C", "H", and "L", for example, and may be rotatable about the subject 110. For example, the gantry rotor 104 may be formed as a closed ring or circle, or as an open arc or arch which allows the subject 110 to be easily accessed while imaging and facilitates loading and unloading of the subject 110, as well as reducing claustrophobia in some subjects 110. For example, in some embodiments the gantry rotor 104 may be arc shaped and the support members 112 movable along the arc to position the detector units 114 at different locations along the gantry rotor 104. In some embodiments, the detector units 114 may also be independently movable along the gantry rotor 104.

Additional imaging detectors (not shown) may be positioned to form rows of detector arrays or an arc or ring around the subject 110. By positioning multiple imaging detectors 102 at multiple positions with respect to the subject 110, such as along an imaging axis (e.g., head to toe direction of the subject 110), image data specific for a larger FOV may be acquired more quickly.

Each of the imaging detectors 102 has a radiation detection face, which is directed towards the subject 110 or a region of interest within the subject 110. The radiation detection faces may be covered by or have coupled thereto a collimator 122. The actual FOV for each of the imaging detectors 102 may be increased, decreased, or relatively unchanged by the type of collimator 122. In one embodiment, the collimator 122 is a multi-bore collimator, such as a parallel-hole collimator. However, other types of collimators, such as converging or diverging collimators may optionally or alternatively be used. Other examples for the collimator 122 include pinhole, parallel-beam converging, diverging fan-beam, converging or diverging cone-beam, multi-bore converging, multi-bore converging fan-beam, multi-bore converging cone-beam, multi-bore diverging, or other types of collimators.

Optionally, multi-bore collimators may be constructed to be registered with pixels of the detector units 114, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in between two adjacent pixels may have reduced sensitivity or decreased energy resolution or other performance degradation. Having collimator septa directly above the edges of pixels reduces the chance of a photon impinging at these degraded performance locations, without decreasing the overall probability of a photon passing through the collimator.

A controller unit 130 may control the movement and positioning of the patient table 120, imaging detectors 102, gantry rotor 104, and/or the collimators 122. A range of motion before or during an acquisition, or between different image acquisitions, is set to maintain the actual FOV of each of the imaging detectors 102 directed, for example, towards or "aimed at" a particular area or region of the subject 110 or along the entire subject 110.

The controller unit 130 may have a gantry motor controller 132, table controller 134, detector carriers controller 136, pivot controller 138, and optional collimator controller 140. It may be understood that in some examples, there may not be a collimator controller, where each collimator is affixed to the corresponding detector during assembly of the detector head. In such an example, detector heads may pivot as one piece comprising the collimator, the CZT detector modules and the shielding. As another example, collimators may be exchanged, for example manually. The controllers 130, 132, 134, 136, 138, (and optionally 140) may be automatically commanded by a processing unit 150, manually controlled by an operator, or a combination thereof. The gantry motor controller 132 may cause a rotation of gantry rotor 104 to rotate in respect to a gantry stator (not shown) about an axis substantially aligned with a center of the camera bore. In some embodiments, the gantry controller 132 may cause rotation of the gantry rotor 104 so that the imaging detectors 102 and/or one or more of the support members 112 rotate about the subject 110, which may include motion of less than or up to 180 degrees (or more).

The table controller 134 may move the patient table 120 to position the subject 110 relative to the imaging detectors 102. The patient table 120 may be moved in up-down directions, in-out directions, and optionally right-left directions, for example. The detector carriers controller 136 may control movement of each of the imaging detectors 102 to move closer to and farther from a surface of the subject 110, such as by controlling translating movement of the detector carriers 116 linearly towards or away from the subject 110 (e.g., sliding or telescoping movement). Said another way, the detector carriers may move radially towards or away from the rotational center of the rotor. Optionally, the detector carriers controller 136 may control movement of the detector carriers 116 to allow coordinated movement of the detector array 106.

The pivot controller 138 may control pivoting, rotating, or swinging movement of the detector units 114 at ends of the detector carriers 116, and/or the detector carrier 116. For example, one or more of the detector units 114 or detector carriers 116 may be rotated or swung about at least one axis to view the subject 110 from a plurality of angular orientations. The optional collimator controller 140 may adjust a position of an adjustable collimator, such as a collimator with adjustable strips (or vanes) or adjustable pinhole(s).

It should be noted that motion of one or more imaging detectors 102 may be in directions other than strictly axially or radially, and optionally, motions in several motion directions may be used. Moreover, the motions of the imaging detectors 102 are coordinated in various embodiments as described herein. Therefore, the term "motion controller" may be used to indicate a collective name for all motion controllers. It should be noted that the various controllers may be combined, for example, the detector carriers controller 136 and pivot controller 138 may be combined to provide the different movements described herein.

Prior to acquiring an image of the subject 110 or a portion of the subject 110, the imaging detectors 102, gantry rotor 104, patient table 120, and/or collimators 122 may be adjusted as discussed in more detail herein, such as to first or initial imaging positions, as well as subsequent imaging positions. The imaging detectors 102 may each be positioned to image a portion of the subject 110. Alternatively, one or more of the imaging detectors 102 may not be used to acquire data, such as the imaging detectors 102 at ends of the detector array 106, which as illustrated in FIG. 1 are in a protracted position towards the subject 110. Positioning may be accomplished manually by the operator and/or automatically, which may include using other images acquired before the current acquisition, such as by another imaging modality such as CT, MM, X-ray, PET, or ultrasound. Additionally, the detector units 114 may be configured to acquire non-NM data, such as x-ray CT data.

After the imaging detectors 102, gantry rotor 104, patient table 120, and/or collimators 122 are positioned, one or more images are acquired by one or more of the imaging detectors 102 being used, which may include pivoting or swinging motion of one or more of the detector units 114, which may pivot, rotate, or swing to different degrees or between different ranges of angles. The image data acquired by each imaging detector 102 may be combined and reconstructed into a composite image, which may comprise two-dimensional (2D) images, a three-dimensional (3D) volume, or a 3D volume over time (4D).

In one embodiment, the imaging detectors 102, gantry rotor 104, patient table 120, and/or collimators 122 remain stationary after being initially positioned. In another embodiment, an effective field of view for one or more of the imaging detectors may be increased by movement such as pivoting (also referred to herein as swinging) one or more of the imaging detectors 102, rotating the detector array 106 with the gantry rotor 104, adjusting one or more of the collimators 122 (where applicable), or moving the patient table 120.

In various embodiments, a data acquisition system (DAS) 160 receives electrical signal data produced by the imaging detectors 102 and converts this data into digital signals for subsequent processing. An image reconstruction device 162 and a data storage device 164 may be provided in addition to the processing unit 150. It should be noted that one or more functions related to one or more of data acquisition, motion control, data processing, and image reconstruction may be accomplished through hardware, software, and/or by shared processing resources, which may be located within or near the imaging system 100, or may be located remotely. Additionally, a user input device 166 may be provided to receive user inputs (e.g., control commands), as well as a display 168 for displaying images.

Additionally, a detector position controller 165 is also provided, which may be implemented in hardware, software, or a combination thereof. For example, as shown in FIG. 1, the detector position controller 165 may form part of or operate in connection with the processing unit 150. In some embodiments, the detector position controller 165 may be a module that operates to control the movement of the imaging detectors 102, including the detector units 114, such that coordinated or synchronized movement is provided as described herein. It should be noted that movement of a plurality of the imaging detectors 102 and/or detector units 114 may be performed at the same time (e.g., simultaneously or concurrently) or at different times (e.g., sequentially or step-wise, such as back and forth between two detector units 114). It also should be understood that when referring to a detector head, such a detector head may include one or multiple detector modules.

As mentioned above, accurate reconstruction of acquired image data requires proper calibration of each of the detector units 114. It may be understood that there may be two classes of calibrations, the two classes referring to "detector-collimator calibrations", and "mechanical calibration." Discussed herein, the detector-collimator calibrations may be used to assign each detector pixel a set of parameters such as energy response (which depends on the CZT pixel and its corresponding electronics). Alternatively, the mechanical calibration correlates the data provided by the motion controller (e.g., rotor motion, detector carrier motion, detector pivot) to the physical location and orientation of the view seen by each pixel. It may be understood that this calibration is governed by the motors and encoders, by assembly imperfections, and to a lesser degree to collimator imperfections. Generally, the two types of calibrations mentioned above do not interact (although they may be performed at the same session). Specifically, a pixel sensitivity will not change when the detector is moved. In contrast, the view seen by a pixel is determined by a combination of all of rotor motion, detector carrier motion and detector pivot motion. As will be discussed herein, systems and methods are provided for mechanical calibration purposes so that a desired image quality may be obtained via the NM system 100 depicted at FIG. 1.

For discussion of the systems and methods for calibration of the detector units, particular axes and plane shifts are referred to. Accordingly, prior to discussion of the methodology for detector unit calibration, explicit reference to the nomenclature of axes and planes discussed herein are described.

Figures 2A, 2B:
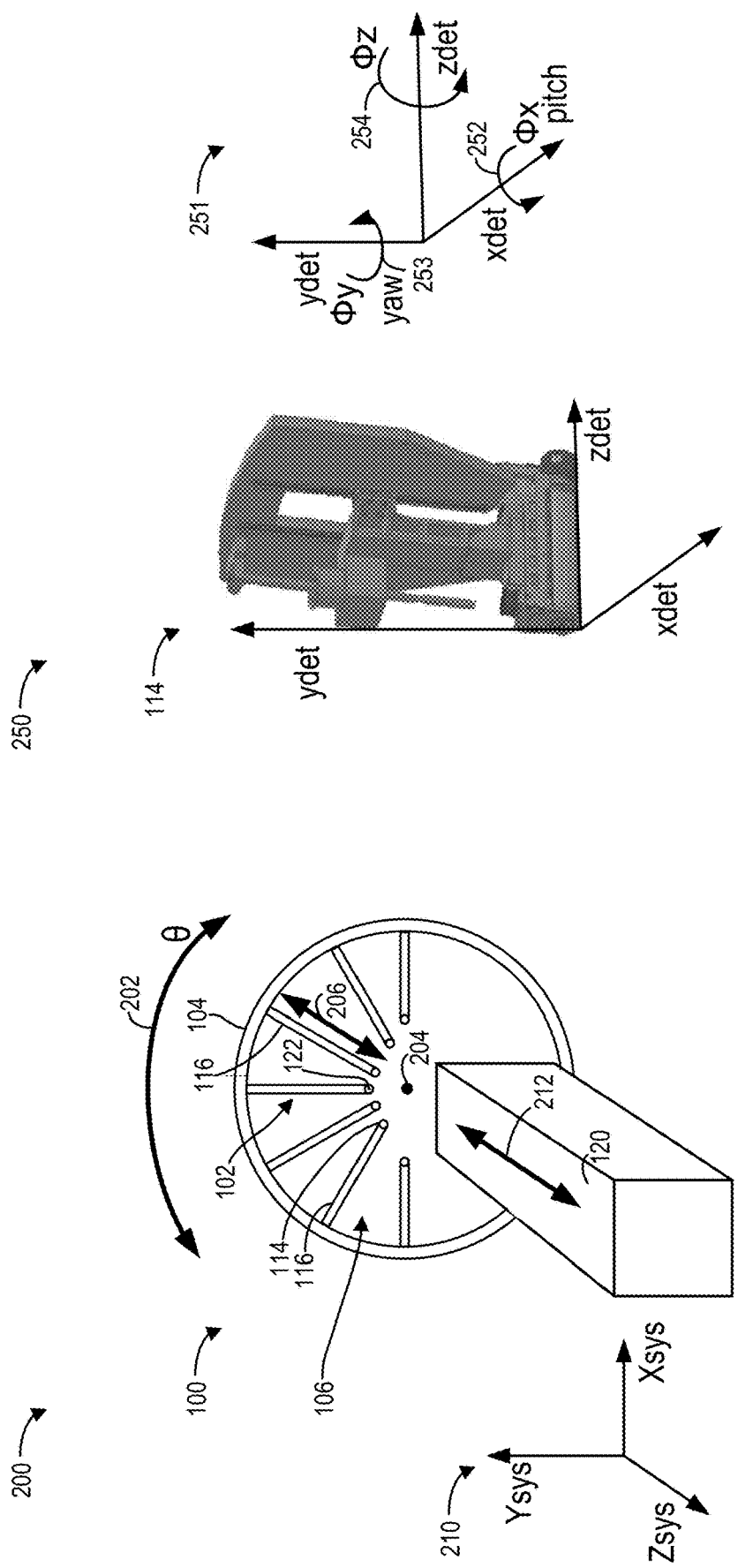
FIG. 2A depicts a portion of the NM imaging system of FIG. 1, and illustrates a rotational axis, a radial axis and a z axis of the NM imaging system in accordance with an embodiment.
FIG. 2B depicts an individual detector unit and corresponding x, y and z axes for the detector unit, in accordance with an embodiment.

Accordingly, turning to FIG. 2A, an example illustration 200 depicts NM system 100 including patient table 120. Discussed herein, rotational motion refers to rotation of gantry rotor 104 with imaging detectors 102 attached around a center of rotation (COR) 204. At FIG. 2A, the rotor's rotation angle (A) is represented by arrow 202. Radial motion, on the other hand, refers to radial movement of individual detector units 114 towards and away from a patient (not shown at FIG. 2A) lying on patient table 120, depicted at FIG. 2A by arrow 206. Discussed herein, patient table 120 can move along a Z-axis (Zsys) (refer to inset 210) of the NM system 100, represented by arrow 212. Inset 210 also depicts an X-axis and a Y-axis (Xsys and Ysys, respectively) of the NM system Turning to FIG. 2B, an example illustration 250 depicts a close-up view of an individual detector unit 114. Discussed herein, it may be understood that each detector unit 114 is defined by x, y and z axes specific to the detector unit (refer to inset 251) (xdet, ydet, and zdet, respectively). It may be understood that ydet is a measure of a distance of a detector unit from the center of rotation 204, and is controlled for each detector unit by the detector carrier controller (e.g., detector carrier controller 136 at FIG. 1). The zdet axis depicted at FIG. 2B is along the same axis as the Zsys-axis depicted at FIG. 2A. Unintentional rotation (due to misalignment) of detector unit 114 about the xdet-axis is referred to herein as pitch ($\phi$xdet), represented by arrow 252. Unintentional rotation (due to misalignment) of detector unit 114 about the ydet-axis is referred to herein as yaw ($\phi$ydet), represented by arrow 253. Discussed herein, movement of detector unit 114 along the xdet-axis and the zdet-axis are referred to as ΔX plane shifts and ΔZ plane shifts, respectively. The motorized pivoting angle $\phi$zdet (refer to arrow 254) is controlled by the pivot controller (e.g., pivot controller 138 at FIG. 1). It should be noted that for each detector, the directions of ydet and xdet may be different, and may change as the rotor is rotated or the detector pivots.

Figure 3A:
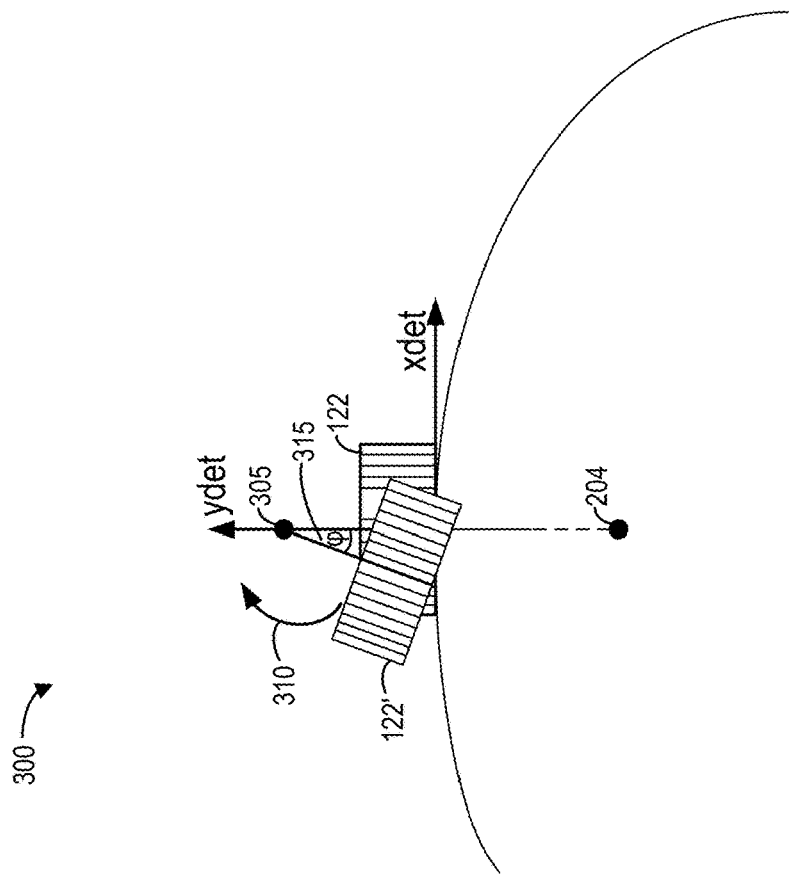
FIG. 3A shows a sweep angle corresponding to a detector unit in accordance with an embodiment.

Turning now to FIG. 3A, an example illustration 300 is shown, illustrating collimator 122 viewed along the zdet-axis (not shown), which is also the Zsys-axis. Depicted at FIG. 3A are the xdet and ydet axes that were referred to above at FIG. 2B. In other words, the xdet and ydet axes at FIG. 3A refer to the x and y axes of the detector unit (e.g. detector unit 114 at FIG. 2B). The center of gantry rotor's rotation 204 is shown, as well as a center of sweep (COS) 305. The collimator 122 may pivot about the COS, as represented by arrow 310. An angle to which the collimator is rotated with respect to the COS is referred to as sweep angle 315, or φ. For example, at FIG. 3A, collimator 122 is depicted at a sweep angle of 0°. Collimator 122' at FIG. 3A shows an example where the sweep angle is not 0°.

Turning to FIG. 3B, example illustration 350 depicts each of 12 detector units when viewed from a point of view of the Xsys-axis. Shown for reference is COR 204, and it may be understood that Zsys (refer to FIG. 2A) is the COR line, and the zdet (for each detector) is parallel to Zsys and COR for any detector sweep angle. Inset 360 depicts the detector units when viewed along the zdet-axis (parallel to the Zsys axis), with the Xsys and Ysys axes depicted for detector unit 12 for reference. When the detector units 1-12 are properly aligned along the zdet axis, it may be understood that all 12 xdet and ydet axes will be aligned with each other and be perpendicular to the COR. Accordingly, dashed line 355 represents a plane that contains xdet and a plane that contains ydet axes. The planes (represented by dashed line 355) should be normal to Zsys. Thus, "proper alignment" means that A) when any detector is at ydet=c (registered by the processor), the distance from COR 204 to COS 305 is the same "c", and B) when sweep angle φ is "0", the line from COS along ydet intersects the center of the detector with respect to both xdet and zdet.

As discussed above, image data acquired by each imaging detector may be combined and reconstructed into a composite image. For the reconstruction process to produce a high-quality image, it has to be known with a high degree of accuracy the location and aiming of each of the detector units. Thus, there are several assumptions made when reconstructing an image. A first assumption is that the zdet axis is parallel to the COS, which is in turn parallel to the COR. In other words, that pitch ($\phi$xdet)=0° and yaw ($\phi$ydet)=0°. For example, pitch may not be measured/corrected, and it may be assumed that the system has passed a mechanical quality control that guarantees the pitch angle within a threshold of 0° (e.g., +/−0.2°). A second assumption is that at a sweep angle (φ) of 0°, projection of a point source placed at the COR will be imaged as a point on the center of the detecetor (in respect to both xdet and zdet). A third assumption is that each of 12 planes, each defined by xdet and ydet of a detector are perpendicular to the line from the COR to the center of the corresponding detector, and are aligned with one another, as discussed with regard to FIG. 3B. If such assumptions are not met, then artifacts may be introduced into the image reconstruction, resulting in degraded image quality.

Turning now to FIG. 4, it depicts a high-level flow chart illustrating an example method 400 for mechanically calibrating a NM imaging system, such as the NM system of FIG. 1. In particular, method 400 relates to a process of aligning each detector unit with the COR of the NM system. In some examples, method 400 may enable simultaneous calibration of detector unit sweep angle offsets of all the detector units (e.g., 12 detector units, in a case where the NM system includes 12 detector units). In other examples, method 400 may enable simultaneous calibration of detector unit sweep angle offsets of less than 12 detector units, for situations where the NM system includes less than 12 detector units. Method 400 will be described herein with reference to the system and components depicted at FIGS. 1-3B, though it should be understood that the method may be applied to other systems without departing from the scope of this disclosure. Method 400 may be carried out by processing unit 150, and may be stored as executable instructions in non-transitory memory of processing unit 150.

Method 400 begins at 405, and includes calibrating a sweep axis of each of the detector units such that at a sweep angle of 0° the projection of the COR on the detector plane is aligned with the z-axis of the detector. Details whereby the sweep axis of each of the detector units may be calibrated in such a manner is discussed with regard to the method of FIG. 5. With the sweep axis of each of the detector units calibrated, method 400 proceeds to 410. At 410, method 400 includes calibrating and correcting the z-axis of each of the detectors such that each of the x and y planes of the detector are aligned with one another and are perpendicular to the COR. Details of step 410 are discussed in greater detail below with regard to the method of FIG. 14. Proceeding to 415, method 400 includes measuring and correcting the x-shift of each of the detector units. Details of step 415 are discussed in greater detail below with regard to the method of FIG. 15. Next, method 400 proceeds to step 420. At 420, method 400 includes measuring and correcting the yaw angle of each of the detectors. Details of step 420 are discussed in greater detail below with regard to the method of FIG. 17.

For the method of FIG. 4, it may be understood that there are several assumptions that may be made in order for the method to be used. For example, a manufacturing process of the NM imaging system of FIG. 1 may be based on an accurate mechanical tool such as a jig. Accordingly, it may be assumed that parts included in the NM imaging system of FIG. 1 are more or less within acceptable tolerance ranges. As an example, it may be assumed that yaw ($\varphi ydet$) and pitch ($\varphi xdet$) for each of the detectors are <0.1°. Another assumption may be that the sweep angle ($\varphi$) of each of the detector units is set, or pre-calibrated to a certain accuracy prior to the application of this calibration process. For example, accuracy should be such that the detector will "see" the point source placed near the COR. As one example, 0.01 radian may be sufficient. Said another way, initial sweep angle may be set by a mechanical level with an accuracy of 0°+/−0.5°. Another assumption may be that the gantry rotor that is used for rotation of the detector array is accurately manufactured to R=400±0.1 mm. Another assumption may be that rotation of the gantry rotor is calibrated by a leveler to ±0.1°. Another assumption may be that radials, that is, the angular deviation of the motion of the carriers (along the actual ydet) from the radial vectors starting at COR and normal to Zsys that intersects the center of each detector, are manufactured or assembled or calibrated to a mechanical machined surface with accuracy of ±0.1°.

Turning now to FIG. 5, it depicts a high-level flow chart illustrating an example method 500 for calibrating a sweep axis of each of the detector units such that at a sweep angle of 0° the projection of the COR on the detector plane is aligned with the z-axis of the detector. As discussed above, method 500 is a sub-method of method 400. Thus, method 500 is described with reference to the system and components depicted at FIGS. 1-3B, though it should be understood that the method may be applied to other systems without departing from the scope of this disclosure. Method 500 may be carried out by processing unit 150, and may be stored as executable instructions in non-transitory memory of processing unit 150.

Method 500 begins at 505, and includes positioning each of the detector units at a same radial distance (refer to arrow 206 at FIG. 2A) from the COR (e.g. COR 204 at FIG. 2A). As one example, each of the detector units may be positioned at intended distance of 135 mm from the COR, however other distances may be selected without departing from the scope of this disclosure. It may be understood that the ydet axis is calibrated at this stage, and the calibration may be done through a motion-mechanical manner. While not explicitly illustrated at FIG. 5, it may be understood that the ydet calibration may be done using a y-LINDEF (Linear Table Axis Definition) calibration that relies on mechanically accurate reference points and levels (spirit level) to set up/reset the position feedback data (e.g., encoder encounters) to a specific physical position or angle. Thus, while not explicitly illustrated, it may be understood that the LINDEF calibration process has to be done on the detector radial axis in the beginning, as well as the rotation axis. The LINDEF calibration of the sweep axis is not of a great enough accuracy, which is herein recognized, and which is the reason for the methodology of FIG. 5.

Figure 6B:
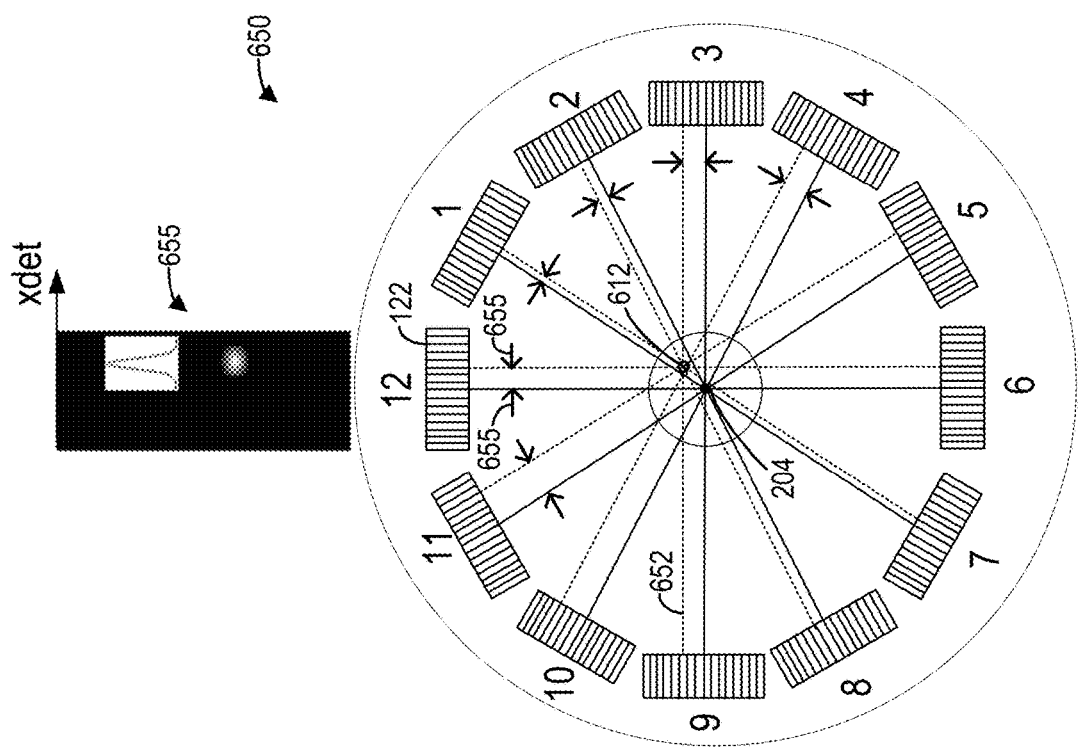
FIG. 6B schematically depicts how center of gravity determinations can be made with respect to the x axis of individual detector units, in accordance with an embodiment.
Figure 6A:
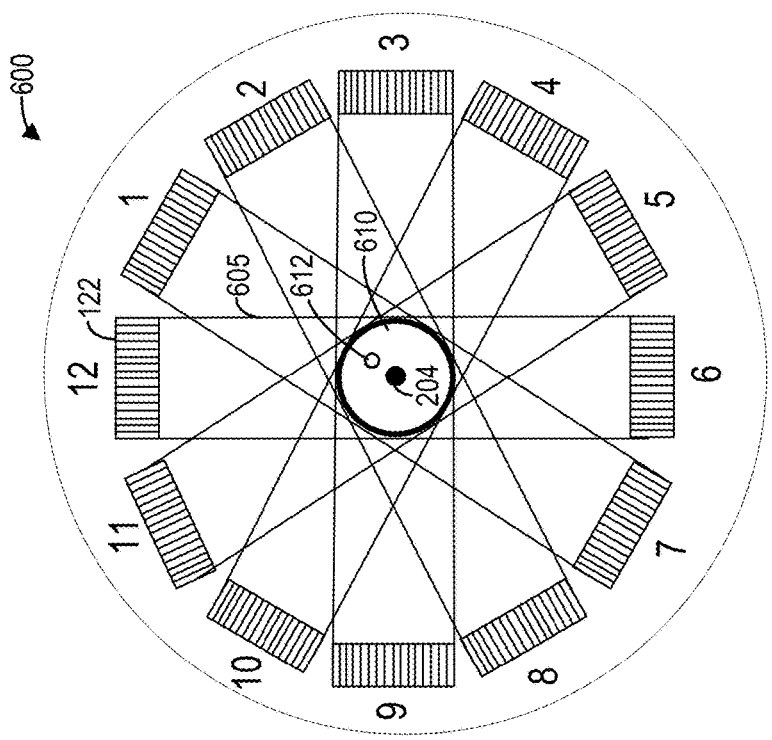
FIG. 6A shows a field of view corresponding to a plurality of detector units, in accordance with an embodiment.

With the detector units each positioned at the roughly same radial distance from the COR, method 500 proceeds to 510. At 510, method 500 includes positioning each of the detector units at an intended sweep angle (($\varphi$) of 0°. Next, method 500 proceeds to 515. At 515, method 500 includes positioning a point source within a field of view (FOV) of each of the detectors. Turning to FIG. 6A, depicted is example illustration 600, showing relative positioning of 12 collimators 122 associated with 12 detector units (1-12). Solid lines 605 are shown connecting opposing collimators thereby defining the joint FOV 610. Depicted in FOV 610 for reference is COR 204. Point source 612 may be positioned within FOV 610 at a position other than COR 204, as depicted at FIG. 6A. It may be understood that the point source may be a gamma radioisotope (e.g., cobalt-57, fluorine-18, gallium-67, krypton-81m, rubidium-82, nitrogen-13, technetium-99m, indium-111, iodine-123, xenon-133, thallium-201, etc.).

With the point source positioned within the joint FOV, method 500 proceeds to 520. At 520, method 500 includes performing a static scan at intended sweep angle (($\varphi$) of 0°, such that each detector captures a projection of the point source over a predetermined number of gantry rotor rotational steps. The predetermined number of rotational steps may be 15 steps, for example, where each step rotationally moves each of the detector units 2° about the rotational axis (refer to arrow 202 at FIG. 2A). Turning to FIG. 6B, depicted is example illustration 650, illustrating a positioning of each of the 12 collimators 122 prior to any rotational steps have been carried out. Depicted is COR 204, and point source 612. Dashed lines 652 depict a projection of point source 612 on each of the 12 collimators. A central of gravity (COG) calculation along the x-axis of the detector units (referred to herein as X_COG) can thus be determined as illustrated by arrows 655 for each of the collimators 122. It may be understood that X_COG refers to where along the xdet axis the point source 612 projects, in relation to a central zero point of the collimator It may be understood that the purpose of the calibration is to set the true value of $\varphi=0°$ such that the projection of a source at COR will be exactly at xdet=0 (central zero point). As illustrated at FIG. 6B, X_COG is greater for detector 12 than for detector 1 prior to any rotational steps having been carried out. For reference, an actual event projection 655 is shown for detector 12 under a situation where point source 612 is positioned as depicted relative to COR 204.

Figure 7A:
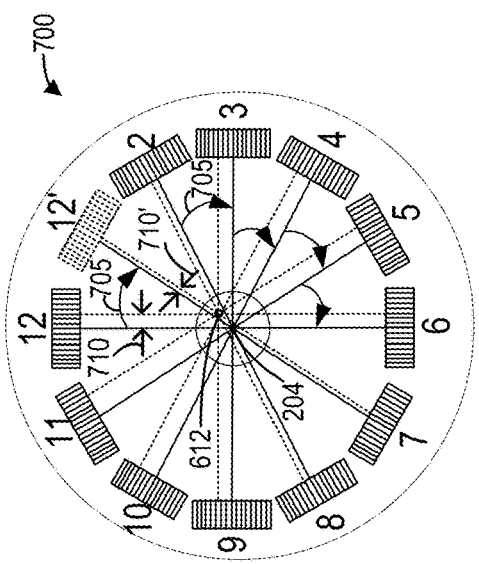
FIG. 7A schematically depicts how center of gravity determinations with respect to the x axis of individual detector units change as the detector units are rotated about a rotational axis of the NM imaging system in accordance with an embodiment.

As discussed, the static scan at 520 is captured over the predetermined number of rotational steps (e.g. 15 steps of 2° for a total rotation of 30°, or in another example, 30 steps of 2° for a total rotation of 60°). Turning to FIG. 7A, example illustration 700 depicts a situation where the first detector is removed to illustratively show how detector 12 is rotated during the static scan. Detector 12 is labeled as "12" to indicate rotational position of detector 12 prior to detector 12 having been rotated, and detector 12 is labeled as 12' to indicate the rotational position of detector 12 after having been rotated the predetermined number of steps (e.g., 15 steps at 2° per step). At FIG. 7A, the change in rotational position of remaining detectors (2-11, where detector 1 is excluded for illustrative purposes) during the static scan is not explicitly depicted, but arrows 705 show how the remaining detectors rotate in similar fashion to that of detector 12 during the static scan. Thus, it may be understood that each detector rotates the predetermined number of rotational steps, each step corresponding to a predetermined number of degrees. As illustratively depicted at FIG. 7A, X_COG for detector 12, represented by arrows 710 and 710' changes during the static scan, such that X_COG is greater prior to the detector unit having been rotated (refer to arrows 710), and becomes lesser as the static scan progresses (refer to arrows 710'). It may be understood that in similar fashion, X_COG for each of the remaining detectors similarly changes during the course of the static scan. In some examples, X_COG decreases (e.g., refer to detector 12) as a result of the rotational movement, whereas in other examples X_COG increases (e.g., refer to detector 8, which rotationally moves to occupy the position illustrated by detector 9) as a result of the rotational movement.

Figure 7B:
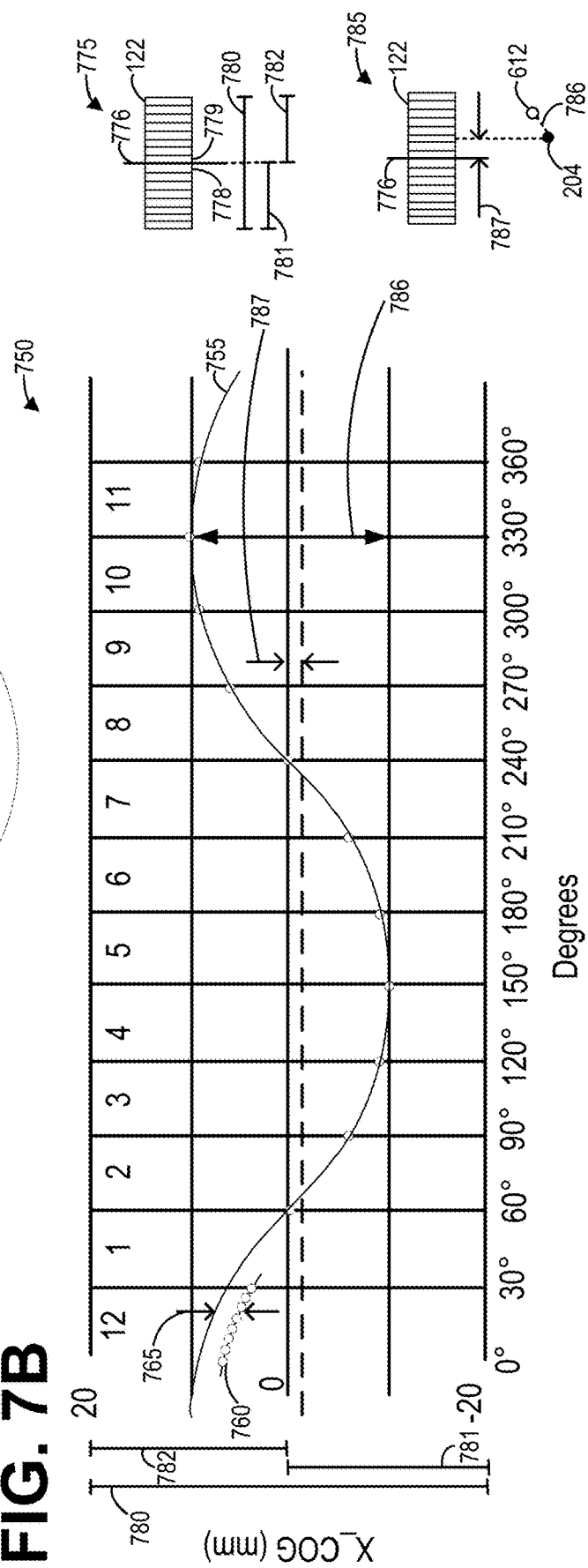
FIG. 7B shows an example graph illustrating a fit corresponding to center of gravity determinations along the x axis of individual detector units obtained via the methodology of FIG. 5, in accordance with an embodiment.

Accordingly, with the projection of the point source acquired by each of the detectors over the course of the static scan, method 500 proceeds to 525. At 525, method 500 includes processing the projections acquired by each of the detectors to determine X_COG corresponding to each rotational step, for each detector. The acquired X_COG data may then be fit to a first order Fourier function. Turning to FIG. 7B, example illustration 750 depicts such a fit.

Example illustration 750 depicts degrees along the x axis, aligned with corresponding detector units 1-12. For example, detector unit 12 rotationally moves during the static scan from a 0° position to a 30° position (e.g., 15 steps of 2° each). In similar fashion, detector unit 1 moves from its initial position at 30° to a position at 60° during the course of the static scan. Remaining detectors also rotationally change position in similar fashion as depicted. The y-axis of illustration 750 depicts X_COG (in mm), relative to a zero point of the collimator. Specifically, inset 775 shows the zero point 776 between row 8 (refer to 778) and row 9 (refer to 779) of collimator 122. Line 780 of inset 775 depicts a length of collimator 122. The length may be 40 mm, for example. Thus, relative to the zero point 776, line 781 represents a length spanning 0 to −20 mm, and line 782 represents a length spanning 0 to 20 mm. For reference, lines 780, 781 and 782 are depicted along the y-axis of illustration 750. It may be understood that such a zero point as referred to with regard to a length of collimator 122 is meant to be representative. For example, it may be understood that in other examples, collimator 122 may be different. Specifically, each detector may include a certain number of pixels and corresponding collimator bores, depending on the application. Regardless of the number of pixels and corresponding collimator bores, the zero point may be selected in similar fashion.

As discussed, the acquired X_COG data may be fit to a first order Fourier function. The first order Fourier function may be of the form:

$$F = A + B\cos(w*\theta) + C\sin(w*\theta); \quad \text{i.}$$

where F is a fitness regression result of interpolated data from n (e.g. 12) detectors over θ (e.g., rotational axis of 30°, refer to arrow 202 at FIG. 2A). Turning to inset 785, "B" and "C" correspond to an amplitude that is approximately equal to a distance 786 between COR 204 and point source 612. "A" corresponds to a DC offset corresponding to an "average" of Δx's between COR 204 and the zero point 776, as represented by arrows 787. A, as well as B and C are graphically shown at illustration 750 (refer to 786 and 787 at illustration 750).

Thus, illustration 750 shows an example fit 755 of acquired X_COG data. Based on the fit, a residual difference (ΔX_COG(θ)i) between measured X_COG (refer to points 760) and the regression interpolated fit 755 can be determined for each detector (i) at each sampled rotation angle (θ). The residual difference (ΔX_COG(θ)$_{12}$) for detector 12 at illustration 750 is depicted by arrows 765. A total ΔX_COGi (total residual difference) per detector may then be determined as an average of (ΔX_COG(θ)) per detector (i).

While not explicitly illustrated at method 500, in some examples method 500 may include optimization of the fitting to obtain improved statistical parameters (e.g. better fit). For example, a detector unit identified to have the greatest residual difference may be removed from the fitting, such that the fitting may be improved.

Figure 8C:
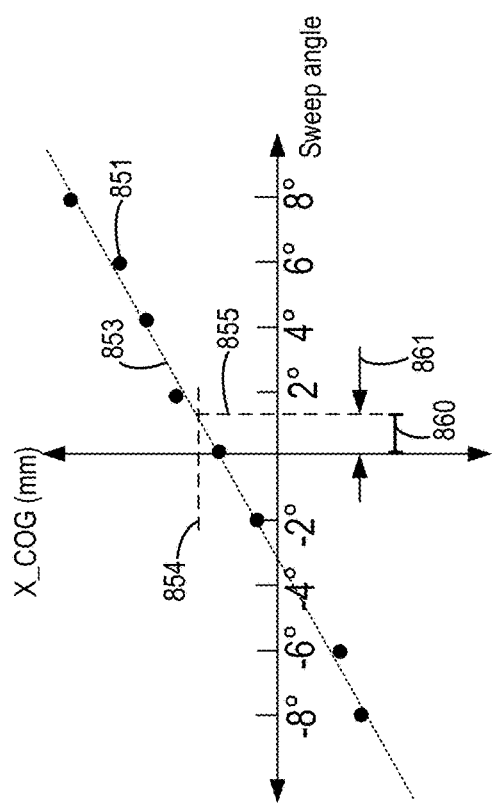
FIG. 8C depicts a graph illustrating how a sweep offset is determined via the method of FIG. 5, in accordance with an embodiment.
Figure 8A:
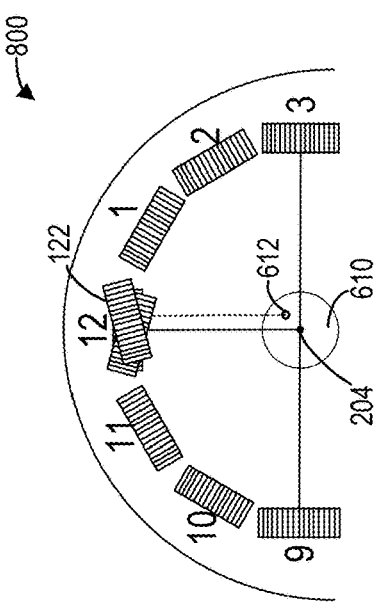
FIG. 8A schematically illustrates different sweep angles for an individual detector unit, in accordance with an embodiment.
Figure 8B:
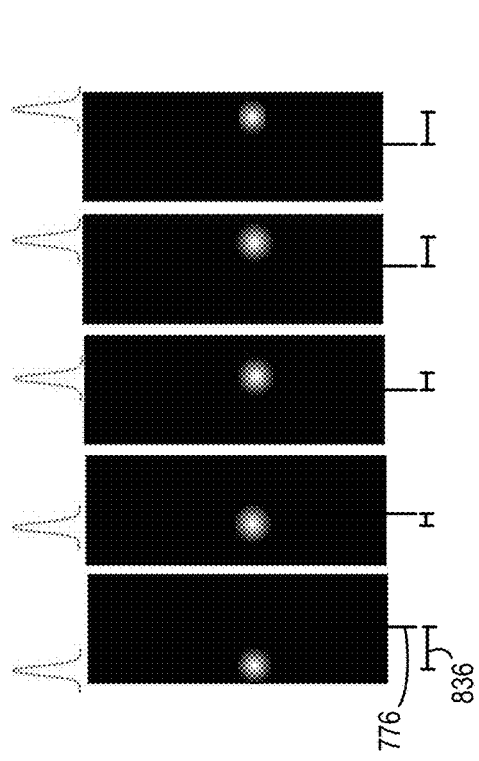
FIG. 8B shows acquired event projections for a particular detector unit along the x axis of the detector unit at different sweep angles, in accordance with an embodiment.

Returning to step 525 at FIG. 5, responsive to the ΔX_COGi per detector "i" having been determined, method 500 proceeds to 530. At 530, method 500 includes maintaining the point source in the same position, and performing a sweep scan to capture the image of the point source at a predetermined number of sweep angles (e.g., sweep angle greater or lesser than 0°) of each of the detector units. Turning to FIG. 8A example illustration 800 depicts a subset of collimators 122, and for illustrative purposes collimator 122 is depicted at three different sweep angles (refer to φ at FIG. 3A). The sweep scan at 530 may include acquiring event projections of the point source for each detector unit at different sweep angles. The sweep angles may include a predetermined number of sweep angles, at predetermined degree steps (e.g., 1° steps, 2° steps, etc.). For example, event projections may be acquired for each detector unit at a first sweep angle, then for a second sweep angle, then for a third sweep angle, and so on. It may be understood that all of the detectors may be controlled to the first sweep angle, and event projections may be acquired for each of the detector units. Then all of the detector units may be controlled to the second sweep angle, and event projections may be acquired for each of the detector units, and so on. Turning to FIG. 8B, illustration 835 depicts an example of actual event projections for a particular detector unit at 5 different sweep angles. As illustrated at FIG. 8B, X_COG 836 differs depending on collimator sweep angle, with respect to the zero point 776. While data corresponding to just one detector unit is depicted at FIG. 8B, it may be understood that similar data may be acquired simultaneously for each detector unit, where each detector unit is controlled to the same sweep angle as discussed above.

The acquired event projection data and resulting X_COG determinations may be stored (e.g., at data storage device 164 at FIG. 1) for later processing (e.g., via processing unit 150 at FIG. 1). Proceeding to 535, method 500 includes processing the projections to determine an offset calibrated sweep angle for each detector unit. Specifically, the X_COG data corresponding to the acquired event projections over the predetermined number of sweep angles may be plotted as a function of sweep angle. Turning to FIG. 8C, example illustration 850 depicts an example plot of sweep angle (x-axis) vs X_COG (mm) (y-axis) for a single detector unit. Filled circles 851 represent X_COG measurements at particular sweep angles. The data may be fit to a specific equation (e.g. $1^{st}$ order Fourier, linear or approximately linear). The fit in this particular example is represented by line 853. Dashed line 854 represents the total residual difference ΔX_COG for the particular detector, calculated as discussed above. Dashed line 855 represents where, along the x-axis, the total ΔX_COG intersects with the fit (line 853) to the data points (filled circles 851). Thus, for the particular detector unit represented at FIG. 8C, a sweep offset 860 may be determined, represented by arrows 861. A similar process may be done for each detector unit, such that a sweep offset for each detector unit may be determined.

Turning to FIG. 9A depicted is an example illustration 900 showing exemplary data acquired for a static scan at sweep angle 0° (top plot), similar to that depicted at FIG. 7B. For the top plot, the x-axis represents degrees of rotation about the rotational axis, and the y-axis represents X_COG. Line 905 represents a fit to the individual data points 910. Residuals (difference between observed values and predicted values) for each of the individual data points 910 are depicted at the bottom plot. FIG. 9B depicts illustration 925, showing sweep offset degree for each of the detector unit, the sweep offset degree determined as discussed above. It may be understood that the 12 detector heads as seen here (and in other figures as depicted herein) are meant to be illustrative and should not be viewed as limiting. For example, as long as there are enough segments of the sinus curve, and as long as the density and distribution of the segments is sufficient to calculate a fit to the sinusoidal curve, then the methodology is expected to work. For example, it may be understood that in one example, the number of detector heads may be more than 5, and less than 20. In another example where just 6 detector heads of 12 are used (e.g., all the even, or all the odd, numbers), then the sinusoidal curve may be estimated in spite of the fact that there may be gaps in the curve. Such may be the case for a camera of lower cost, or for use with small subjects (e.g., infants, brain, etc.). In a related example, such methodology may be useful when one or more detector heads are missing, or are non-functional. As yet another related example, if just six or seven (or more) contiguous (e.g., heads 1-7) heads are used (e.g., in a camera tailored for cardiac imaging), the sinusoidal curve may similarly be estimated without departing from the scope of this disclosure.

Figure 9C:
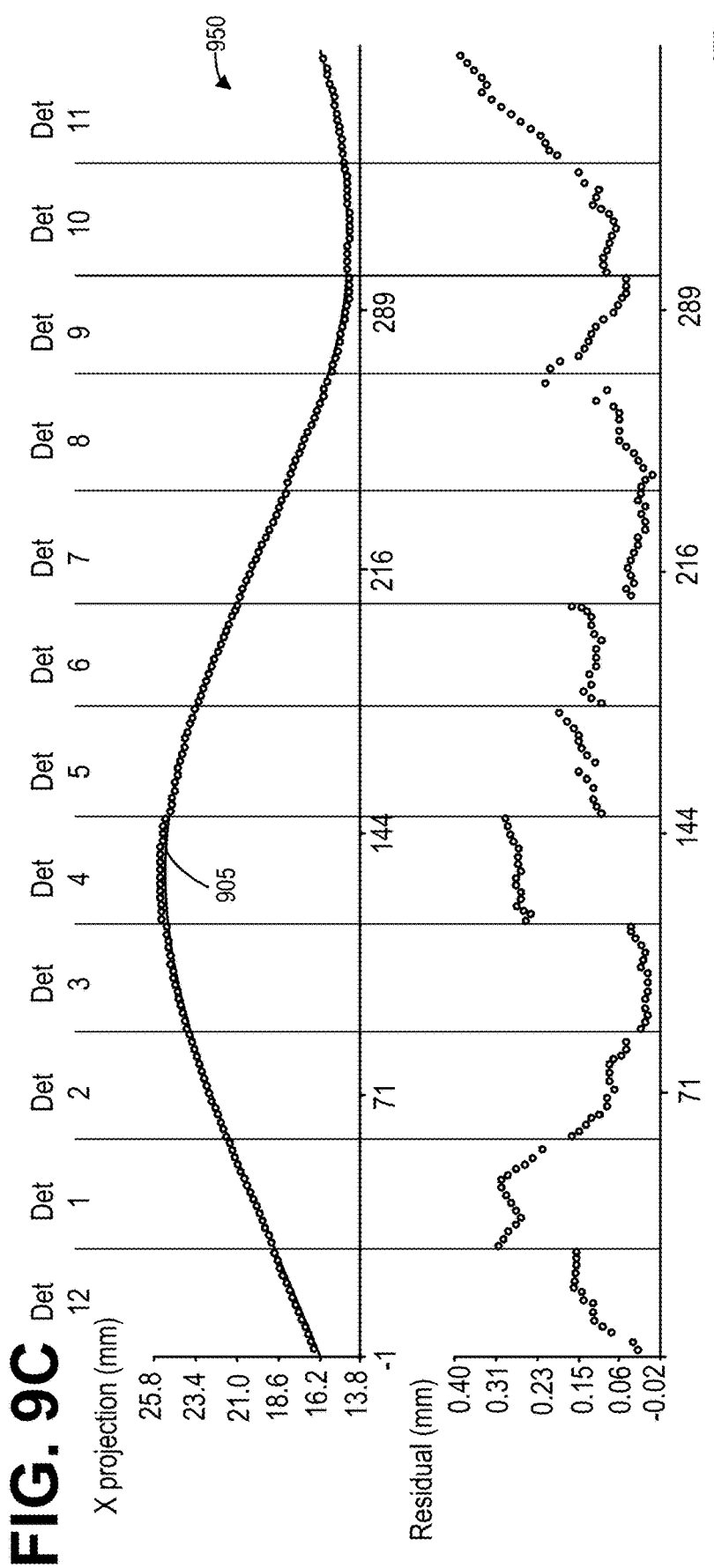
FIG. 9C depicts a graph illustrating how the sweep axis zero position of detector units are corrected by the sweep offset measured, in accordance with an embodiment.
Figure 9D:
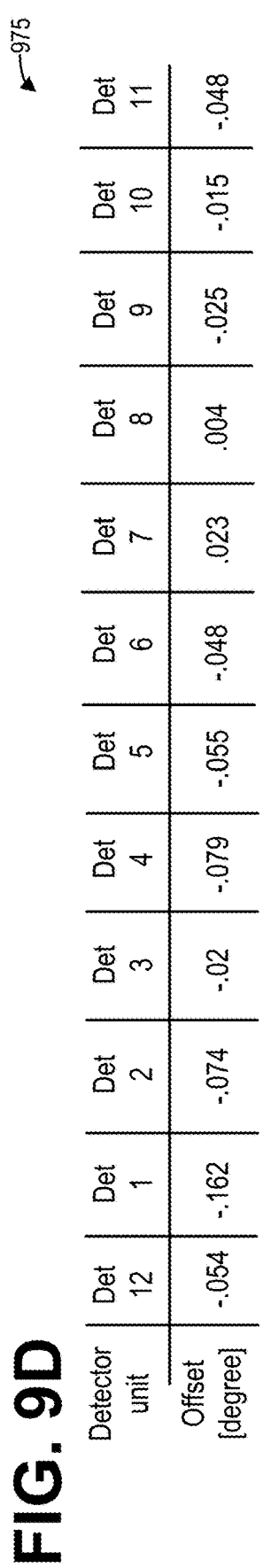
FIG. 9D depicts residuals corresponding to the graph of FIG. 9C, in accordance with an embodiment.

With the sweep offset degree determined for each of the detector units, method 500 proceeds to step 540. At 540, method 500 includes correcting the sweep axis 0° position of each detector unit by the sweep offset degree measured. Turning to FIG. 9C, example illustration 950 depicts the same plot as that of plot 900 at FIG. 9A, illustrating how the sweep axis zero position of each detector unit is corrected by the offset measured. FIG. 9D depicts illustration 975, showing the corrected sweep offset degree.

Figure 10:
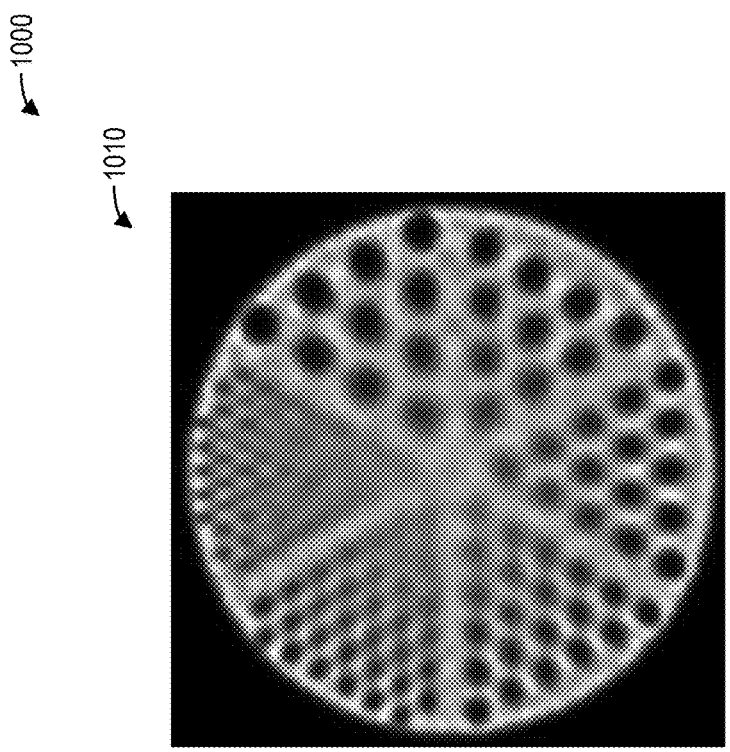
FIG. 10 depicts an example image quality test in accordance with an embodiment.
Figure 10:
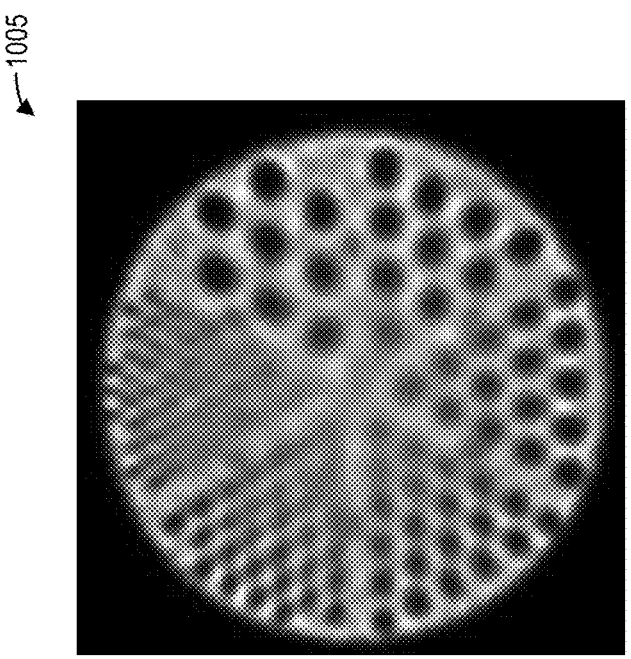

With the sweep axis 0° position of each detector corrected, method 500 proceeds to 545. At 545, method 500 includes performing an image quality test (e.g. Jaszczak Phantom test) to ensure that the correction procedure outlined above produces actual images of a desired quality. Turning to FIG. 10, example illustration 1000 depicts an image quality test. The first image 1005 on the left is an actual SPECT scan of a Jaszczak obtained by using the calibration methodology discussed above with regard to FIG. 5. The second image 1010 on the right is a simulated image, the simulation relying on same parameters as that used for acquiring the actual image 1005. The calibration procedure of FIG. 5 results in a high quality image being obtained, in good accordance with the simulation.

It is herein recognized that the process discussed above with regard to FIG. 5 may not be limited to a single radial axis (refer to step 505 of method 500 at FIG. 5), but instead the sweep angle ((p) may be calibrated over the entire radial range (refer to arrow 206 at FIG. 2A) of detector unit motion. Accordingly, turning now to FIG. 11, a high-level example method 1100 is shown, depicting process steps for calibrating the sweep angle over an entire (or in other examples a subset) radial range of the NM imaging system. Method 1100 will be described with reference to the system and components depicted at FIGS. 1-3B, though it should be understood that the method may be applied to other systems without departing from the scope of this disclosure. Method 1100 may be carried out by processing unit 150, and may be stored as executable instructions in non-transitory memory of processing unit 150.

Method 1100 begins at 1105, and includes repeating the process of FIG. 5 at a predetermined number of radial positions. For example, the process of FIG. 5 may be first conducted at a radial position of 100 mm, then 150 mm, then 200 mm, then 250 mm, then 300 mm, etc. Of course, other sequences of radial positions are within the scope of this disclosure.

Proceeding to 1110, method 1100 includes for each radial position tested, calculating a sweep offset for each detector unit. Then, at 1115, method 1100 includes determining an extrapolated calibration factor over all radials for each detector unit.

Turning to FIG. 12, an example illustration 1200 is shown, depicting a graph of sweep offsets ($\Delta\varphi$) (y-axis) determined as a function of radial length (mm) (x-axis). In this example illustration 1200 the process of determining sweep offsets was conducted at radial positions of 135 mm, 200 mm, 250 mm, 300 mm, and 350 mm. Data points 1205 show the sweep offsets determined at each of the tested radial positions. Extrapolated calibration factor 1210 represents a fit (e.g., linear) to the data acquired by each detector. In this way, for any radial distance, sweep offset may be calculated. Such extrapolations may be needed if the carriage is not traveling exactly along the radial direction, or is otherwise imperfectly constructed or assembled.

Thus, discussed above, the method of FIG. 5 (and in some examples in conjunction with the method of FIG. 11) enables calibration of the detector unit sweep axes such that for each detector unit, the projection of the COR on the detector plane at a sweep angle 0° is aligned with the z-axis of the detector. While the discussion of FIG. 5 centered on positioning the point source within the FOV, it is herein recognized that in other examples, the point source may be positioned at any location within a circumference of the plurality of detectors, without departing from the scope of this disclosure. In such an example, the X_COG measurements may be fit to a higher order function, rather than the first order Fourier function as discussed above.

Discussed herein, it may be understood that acquisitions of the point source may be conducted in a "step and shoot" manner, or a continuous manner, without departing from the scope of this disclosure. For example, in a "step and shoot" methodology, during a "step" at least one detector is moved in at least one degree of motion (e.g., change the sweep angle), and during a "shoot" aspect an image is acquired. In such an example, each image is associated with the location of the detector at the time of shooting. This is in contrast to "continuous shooting", which can be used instead of a step and shoot mode with regards to the methodology discussed herein. Continuous shooting refers to a mode in which at least one detector is continuously moving (slowly and steadily) while data is continuously acquired. The acquired data may then be segmented into different views, where each view is associated with an average location of the detector during the motion taken in the view. A disadvantage of continuous shooting may be some blurring of the image. However, an advantage may be shorter acquisition time compared to a step and shoot mode where data is not collected during detector motion.

Returning to FIG. 4, responsive to the calibration of the detector unit sweep axes at step 405, method 400 proceeds to 410. As discussed, step 410 includes calibrating and correcting the z-shift offset of each of the detector units. Accordingly, turning now to FIG. 13, a high-level example method 1300 is shown, depicting process steps for calibrating and correcting the z-axis of the detector units. As discussed above, with regard to FIG. 3B, when detector units are properly aligned along the zdet axis, each of the detector x and y planes (e.g. xdet and ydet) will be aligned with each other and be perpendicular to the COR. If such misalignment conditions are not accounted for, degraded image quality may result. Thus, method 1300 may be understood to comprise a method for calibrating the detector units to confirm that the x and y planes of each detector are aligned and perpendicular to the COR. Method 1300 will be described with reference to the system and components depicted at FIGS. 1-3B, though it should be understood that the method may be applied to other systems without departing from the scope of this disclosure. Method 1300 may be carried out by processing unit 150, and may be stored as executable instructions in non-transitory memory of processing unit 150. With regard to the method of FIG. 13, it may be understood that just the calculation steps (see steps 1320-1335) may be different from the methodology of FIG. 5. Said another way, once steps 505-520 of method 500 have been carried out, then the data can be used for both the methodology of FIG. 5 and FIG. 13. However, for clarity, steps 1305-1315 are additionally depicted at FIG. 13.

Method 1300 begins at 1305, and includes positioning a point source at an arbitrary position in the FOV, similar to that described above with regard to step 515 of method 500. Proceeding to 1310, method 1300 includes positioning each of the detector units at a same radial position (e.g. 200 mm) (refer to arrow 206 at FIG. 2A), and positioning each of the detector units at a sweep angle of 0°. Turning to FIG. 14A, depicted is an example illustration 1400, showing placement of the point source 612 in FOV 610. COR 204 is depicted for reference within FOV 610. Illustration 1400 is substantially similar to illustration 650, and thus for brevity exhaustive description of illustration 1400 is not reiterated. However, the difference between illustration 650 and illustration 1400 is that the event projection is determined along the zdet axis (refer to FIG. 2B) at illustration 1400, as opposed to along the xdet axis at illustration 650. Said another way, method 1300 includes determining Z_COG (zdet central of gravity), which may be understood to be where the point source projects along the z axis of the detector unit.

Turning to FIG. 14B, it depicts example illustration 1430, showing detectors 12 and 6 (corresponding to detectors 12 and 6 of FIG. 14A), when viewed along the xdet axis (for reference refer to FIG. 2B). Placement of point source 612 is depicted, and dashed line 1435 represents COR 204 (refer to FIG. 3B). Point source event projections 1440 are shown to illustrate where along the zdet axis the point source projection is detected. For illustrative purposes, example illustration 1430 depicts a situation where the detector units are aligned along the zdet axis, such that Z_COG is the same for both detector 12 and detector 6. However, in the event that detector 12 and detector 6 are offset along the zdet axis to some degree, Z_COG may differ between detector 12 and detector 6, as will be elaborated in further detail below. As will be discussed below, the determination of Z_COG may depend on a knowledge of the length 1445 of the detector unit along the zdet axis. In some examples the length 1445 of the detector unit along the zdet axis may be 280 mm, although length 1445 may be greater or lesser than 280 mm without departing from the scope of this disclosure.

Returning to FIG. 13, with the point source positioned in the FOV and with each of the detectors at sweep angle 0° and positioned at the same radial distance, method 1300 proceeds to 1315. At 1315, method 1300 includes performing a static scan such that each detector unit captures a projection of the point source over a predetermined number of rotational steps (e.g., 15 steps of 2° each). Step 1315 is thus similar to step 520 discussed above with regard to method 500 at FIG. 5, with the exception that the data obtained relates to the projection of the point source along the zdet axis, as opposed to the xdet axis of the detector unit.

Proceeding to 1320, method 1300 includes determining Z_COG per detector unit for each rotational step. Turning to FIG. 14C, an example illustration 1450 is shown, depicting rotational degrees on the x-axis as a function of detector unit (1-12). Z_COG is depicted along the y-axis. For reference, length 1445 of the detector unit along the zdet axis is shown. In this example illustration 1450, the length of the detector unit along the zdet axis is 280 mm as shown.

Thus, based on illustration 1450, it may be understood that each of the detector units rotationally moves above the rotational axis (refer to 202 at FIG. 2A) 30° during the course of the static scan. At each rotational step, data pertaining to the event projection of the point source in relation to the zdet axis is acquired for each detector unit. Based on the acquired data, Z_COG is determined for each rotational step for each detector unit. For illustrative purposes, a subset of the calculated Z_COG determinations 1455 is shown for detector units 12, 1 and 2. For remaining detectors 3-11, a single Z_COG determination is shown, which may be understood to represent an average of the Z_COG determinations collected over the 30° rotational movement for each detector unit.

Returning to FIG. 13, responsive to Z_COG being determined at each step for each detector unit, method 1300 proceeds to 1325. At 1325, method 1300 includes calculating a median, or the average, of all Z_COG measurements (refer to 1455). Returning to FIG. 14C, line 1460 represents the median of all Z_COG data. Discussed herein, median 1460 may also be referred to as Zp_COG.

Returning to FIG. 13, with Zp_COG determined, method 1300 proceeds to 1330. At 1330, method 1300 includes calculating an absolute value of a difference between an average of Z_COG determinations (where the average is referred to herein as Zi) for each detector unit and the median (Zp_COG). Turning to FIG. 14C, this value may be understood to represent a z-shift offset 1465 for each detector unit.

Returning to FIG. 13, with the z-shift offset determined for each detector unit, method 1300 proceeds to 1335. At 1335, method 1300 includes reporting the z-shift offset values determined for each detector unit to software in order to update NM imaging system parameters for correct planar and SPECT reconstruction images. For example, reconstructed images may be shifted via the z-offset to guarantee alignment between a physical position of the point source and z-coordinates at each detector plane. Method 1300 may then end.

Thus, discussed above, the method of FIG. 13 enables measurement of the z-shift for each detector unit, and thereby image correction (e.g. image shifting) in a manner whereby all detector units are aligned along the z-axis. Returning to FIG. 4, responsive to the calibration of the detector unit z-axis, method 400 proceeds to 415. At 415, method 400 includes measuring and correcting the x-shift of each of the detector units. Accordingly, turning now to FIG. 15, a high-level example method 1500 is shown, depicting a process flow for measuring and correcting the x-shift of each of the detector units. Briefly, it may be understood that it may be desirable to obtain both the sweep angle calibration (step 405) and the x-shift calibration (step 415). Briefly, it may be understood that the effect of sweep non-calibrated and x-shift are the same on the perpendicular projection of the point source on the detector plane. Thus, in terms of calibrating sweep, it may be that calibration may comprise a composition of both inaccuracies. It may be understood that it is not trivial to differentiate both axes non-calibrated with a single source. Thus, no x-shift is assumed for the sweep calibration, and then the x-shift is checked secondly.

Method 1500 will be described with reference to the system and components depicted at FIGS. 1-3B, though it should be understood that the method may be applied to other systems without departing from the scope of this disclosure. Method 1500 may be carried out by processing unit 150, and may be stored as executable instructions in non-transitory memory of processing unit 150.

Method 1500 begins at 1505, and includes positioning a point source at an arbitrary position in the FOV, similar to that discussed above. In some examples, positioning the point source at 1505 may include maintaining the point source at the position the point source was placed for correcting detector unit sweep angles (FIG. 5), and/or for determining detector unit z-shifts (FIG. 13). With the point source positioned at 1505, method 1500 proceeds to 1510. At 1510, method 1500 includes positioning each detector unit to a sweep angle 0°. While not explicitly illustrated, in some examples method 1500 at step 1510 may include controlling each detector unit to the same radial position. However, in other examples, each detector unit may not be controlled to the same radial position, without departing from the scope of this disclosure.

Continuing to 1515, method 1500 includes performing a static scan such that each detector captures a projection of the point source over a predetermined number of rotational steps. Then, at 1520, method 1500 includes calculating X_COG from a reference point (e.g., zero point) on each detector unit. With X_COG determined for each detector unit, method 1500 proceeds to 1525, and includes calculating the x-shift offset based on the X_COG measurements and point source coordinates. Steps 1520 and 1525 are discussed in greater detail with regard to FIGS. 16A-16B. Turning to FIG. 16A, it depicts an example illustration 1600 showing a portion of the NM imaging system of FIG. 1, illustrating detector units 1-3 and 9-12. Also depicted is COR 204, and point source 612. Point source coordinates 1605 are shown as $X_0$, $Y_0$. Dashed line 1608 illustrates a projection of point source 612 onto detector unit 12. While not explicitly illustrated for remaining detector units, it may be understood similar to that discussed above that each detector unit receives a projection from point source 612. FIG. 16B shows an example illustration 1635, depicting COR 204, and point source 612, along with collimator 122 corresponding to a representative detector unit. The reference point (refer to step 1520) is illustrated by arrow 1636. The reference point may be a midpoint along the xdet axis of the collimator, for example. Arrow 1637 shows $X_0$, or in other words, the point source coordinate corresponding to the x-axis of the detector unit. Dashed line 1608 illustrates the projection of point source 612 onto the collimator, similar to that illustrated at FIG. 16A. Arrow 1638 illustrates an example X_COG determination, which is a distance (e.g., mm) between the reference point (represented by arrow 1636) and where along the collimator the $X_0$ point source coordinate projects. The x-shift (refer to arrows 1640) is thus a difference between $X_0$ (arrow 1637) and X_COG (arrow 1638).

While FIGS. 16A-16B depict a single collimator associated with a single detector unit, it may be understood that the x-shift for each detector unit may similarly be obtained for remaining detector units. Returning to FIG. 15, in response to the x-shift being determined for each detector unit at a sweep angle ($\varphi$) of 0°, method 1500 proceeds to 1530. At 1530, method 1500 may include repeating steps 1510-1525 for a predetermined number of sweep angles (e.g., sweep angle≠0°), in order to improve accuracy of the x-shift offset determination. Turning to FIG. 16C, example illustration 1675 shows an example of such a sweep angle that is not 0°.

Other than the sweep angle being different that that depicted at FIG. 16B, the description of how the x-shift is calculated is similar, and will not be reiterated for brevity. However, it may be understood that determining the x-shift at a number of different sweep angles may enable an improvement in terms of accuracy to the x-shift determination. For example, any number of x-shift measurements may be obtained and averaged together so as to obtain a high confidence x-shift measurement corresponding to each detector unit. Returning to FIG. 15, step 1530 is dashed, to illustrate that the step may be optional. In other words, the x-shift may in some examples simply be determined at a single sweep angle (e.g., 0°), without relying on a number of other measurements of x-shift at different sweep angles, without departing from the scope of this disclosure.

With the x-shift for each detector unit determined, method 1500 proceeds to 1535. At 1535, method 1500 includes reporting the x-shift offset of each detector unit to the software to update system parameters for correct planar and SPECT reconstruction images. For example, reconstructed images may be shifted via the x-shift offset to guarantee alignment between a physical position of the point source and z-coordinates at each detector plane Method 1500 may then end.

Thus, discussed above, the method of FIG. 15 enables measurement of the x-shift for each detector unit, and thereby image correction (e.g., image shifting) in a manner whereby all detector units are aligned along the xdet axis. Returning to FIG. 4, responsive to measuring and correcting the x-shift offset for each of the detector units, method 400 proceeds to 420. At 420, method 400 includes measuring and correcting the yaw angle of each of the detectors. Referring to FIG. 2B, the yaw angle is referred to by arrow 253, corresponding to rotation of a detector unit about its ydet axis. Accordingly, turning now to FIG. 17, method 1700, a high-level example method 1700 is shown, depicting a process flow for measuring and correcting for a yaw-shift of each of the detector units. Correcting the yaw-shift may be understood to be such that the x,y planes (e.g., xdet, ydet) of each detector unit are aligned with each other and are perpendicular to the COR. Method 1700 will be described with reference to the system and components depicted at FIGS. 1-3B, though it should be understood that the method may be applied to other systems without departing from the scope of this disclosure. Method 1700 may be carried out by processing unit 150, and may be stored as executable instructions in non-transitory memory of processing unit 150.

Method 1700 begins at 1705, and includes positioning a point source within the FOV of each of the detectors, similar to that discussed above. In some examples, the point source may already be positioned in the FOV, and in such an example the point source position may be maintained. In other examples, the point source may be positioned at an arbitrary position within the FOV of each of the detector units, without departing from the scope of this disclosure.

Proceeding to 1710, method 1700 includes positioning each detector unit to a predetermined sweep angle (e.g. 0°). While not explicitly illustrated, at 1710 method 1700 may include positioning each detector unit at a same predetermined radial distance. Continuing to 1715, method 1700 includes the steps of moving the patient table (e.g., 120) in the z direction (refer to arrow 212 at FIG. 2A) in single steps of predetermined length, and acquiring a point source projection for each of the detector units at each step. The number of steps and the predetermined length of each step may be selected by an operator of the NM imaging system, or may be preset.

Proceeding to 1720, method 1700 includes calculating X_COG for each step, similar to that discussed above, for each of the plurality of detector units. Continuing to 1725, method 1700 includes graphing X_COG vs the z position of the patient table, for each detector unit. Based on the graph, at step 1730, method 1700 includes determining a yaw angle for each detector unit. Turning to FIG. 18, an example illustration 1800 is depicted, illustrating such a graph for an example detector unit. The graph depicts a z-axial length (in mm) on the x-axis, and X_COG (in mm) along the y-axis. Individual data points 1805 illustrate X_COG measurements for each step of the patient table along the z-axis. The data is fit (illustrated by line 1810) to an equation of the form y=mx+b, where m is the slope of the line and b is the y-intercept. In an alternative representation, two or more point sources may be placed such that the distance between them is known and is in the direction essentially parallel to Zsys (for example, a bar having two or more point sources embedded in it at known distance from each other). Using this method, similar data as that discussed at FIG. 17-FIG. 18 may be obtained, without bed movement.

Returning to FIG. 17, with the yaw angle thus determined for each detector unit by the process depicted illustratively at FIG. 18, method 1700 proceeds to 1735. At 1735, method 1700 includes reporting the yaw angle of each detector unit to software to updated system parameters for correct planar and SPECT reconstruction images. Method 1700 may then end.

Thus, with regard to the method of FIG. 5, it may be understood that the sweep angle calibration is done first, with the point source near the middle of zdet. Once the sweep angle calibration is done, a point source at COR may be seen at xdet=0 when y=0. However, if the detector is unintentionally rotated in yaw, then a point on the Zsys line, away from the COR, may appear shifted in xdet when y=0. To calibrate the yaw, the method of FIG. 17 includes moving the source in the z direction using the bed.

Returning now to the method of FIG. 5, as discussed above, step 525 of method 500 may in some examples include optimization of the fitting to obtain improved statistical parameters. For discussion purposes, the fitting is herein evaluated from three different perspectives.

As one example, in the event that a particular detector unit (e.g., detector unit 12) is found to be mis-calibrated (e.g., the X_COG offset differs from the expected X_COG (refer to arrows 765 at FIG. 7B) by more than a threshold based on the fitting that included the mis-calibrated detector unit), then better statistical parameters may result when the mis-calibrated detector unit is not included in the regression analysis. For example, SSE (sum of squared residuals) and $R^2$ parameters may be improved by such exclusion of a mis-calibrated detector unit.

As another example, the rotational steps for the method of FIG. 5 were discussed above as being 2° (e.g., 15 steps of 2° each). However, it is herein recognized that steps of different degrees may be used, without departing from the scope of this disclosure, and in some examples, without affecting quality of the fitting and resultant statistical parameters. For example, rather than relying on 2° steps, 6° steps may be used. While not explicitly shown, the use of 6° steps may not result in a degraded fitting of X_COG as a function of rotational angle for each of the detector units, but may reduce the time it takes to acquire the X_COG data significantly. For example, relying on steps of 6° rather than 2° may reduce the time for acquiring point source projections (refer to step 520 of method 500, for example) by roughly 20 minutes.

As another example, while the above methodology with regard to FIG. 5 was discussed in terms of a NM imaging system having 12 detector units, it is herein recognized that a similar process may be conducted for NM imaging systems that have different numbers of detectors arranged about the gantry. As one example, a NM imaging system may include 6 detector units arranged 60° apart from one another. Turning to FIG. 19A, such an imaging system is depicted by illustration 1900, showing each detector unit 1905 positioned 60° about the rotational axis from one another. In such an example, rather than rotating each detector unit 30° (e.g., 15 steps of 2° each, or 5 steps of 6° each), each detector unit may be rotated 60° (e.g., 10 steps of 6°, 30 steps of 2°, etc.), as depicted by arrow 1910. However, in other examples, even when the NM imaging system includes 6 detector units arranged 60° apart from one another along the rotational axis, the detector units may be rotated a total of 30° (e.g., 15 steps of 2° each, 5 steps of 6° each, etc.), without departing from the scope of this disclosure. Furthermore, other system configurations are within the scope of this disclosure, where the method of FIG. 5 can be used. For example, consider a NM imaging system that includes 7 detector units, each positioned 30° from one another, with two of the detector units positioned 150° from one another. Turning to FIG. 19B, such an imaging system is depicted by illustration 1930. In one such example, the method of FIG. 5 may be used with a 60° rotational step (e.g., 10 steps of 6°), as indicated by arrow 1935. Arrow 1936 thus represents a portion along the rotational axis where X_COG measurements may not be obtained. For such an example, it may be possible to fit the data in similar fashion as that discussed in detail above with regard to FIG. 5. Graph 1930 depicts one such example. Graph 1930 depicts rotational degrees on the x-axis, and X_COG measurements on the y-axis, similar to that depicted at FIG. 7B. Individual example X_COG measurements 1940 for the detector units are shown. Line 1942 illustrates a region where X_COG measurements are not obtained, the region corresponding to arrow 1936. Solid line 1948 depicts a fit (e.g., sinusoidal first order Fourier function) to the X_COG measurements, and dashed lines 1949 show a 95% prediction interval.

While illustration 1930 depicts a region where X_COG measurements are not obtained, it may be understood that in other examples, such a gap or region may be filled by imaging while rotating the rotor by a greater total amount in order to cover a larger range. This may avoid the gap for cases such as that depicted illustratively at FIG. 19B, and may be understood to even be used in cases such as that depicted above at FIG. 9A, such that overlap may be used to improve the fit to collected data points. A technical effect of the disclosure includes alignment of each detector unit to the center of rotation of the nuclear medicine imaging system.

Another technical effect of the disclosure is simultaneous calibration of sweep offsets of a plurality of detectors (e.g., 12 detectors). Another technical effect of the disclosure is that the systems and methods disclosed herein overcome a limited gantry rotation angle of <180° of the system, due to the fact that a minimum required rotation angle of this disclosure is 30 degrees. Still another technical effect of the disclosure is that the calibration methodology disclosed herein does not require an accurate position of the radioactive calibration point source. For example, in a case where the point source is positioned within a sphere of diameter equal to detector width, the X_COG fit may be via a first order Fourier function. However, it is herein recognized that the point source can be positioned anywhere inside the detectors circumference and the X_COG fit may be via a higher order function. Still another technical effect is that the sweep offset correction methodology may be conducted similarly in situations where the number of detectors is less than 12 and/or under circumstances where the detector units are not distributed uniformly around the gantry.

Turning now to FIG. 20, depicted is a high-level flow chart illustrating an example method 2000 for performing a geometric calibration procedure for an NM imaging system, such as the NM imaging system of FIG. 1. Method 2000 will be described herein with reference to the system and components depicted at least at FIG. 1 and FIG. 21 below, though it should be understood that the method may be applied to other systems without departing from the scope of this disclosure. At least parts of method 2000 may be carried out by processing unit 150, and may be stored as executable instructions in non-transitory memory of processing unit 150.

Method 2000 begins at 2005, and includes placing an apparatus that comprises a linear array of equidistant radioactive point sources, and a Styrofoam object, roughly parallel to the COR axis (see for example 204 at FIG. 3B). It may be understood that this may enable the generating of a contour to be used to define the scan. Specifically, it may be understood that the linear array of equidistant radioactive point sources may transect the Styrofoam object. The radial position of the detector may be determined by the contour of the Styrofoam which may be equal or more than 20 cm. Turning to FIG. 21, illustration 2100 shows a substantially similar illustration as that depicted at FIG. 2A, with like numerals for reference. Further depicted at FIG. 21 is an example of the linear array of equidistant radioactive point sources 2105. Each of the equidistant radioactive point sources may be connected together by a rigid connecting element 2106. Further depicted is Styrofoam object 2107. It may be understood that FIG. 21 thus depicts the linear array of equidistant radioactive point sources 2105 that are diagonal relative to the FOV, and the Styrofoam object 2107 at a position roughly parallel to the COR axis. This setup as depicted may enable at least two points to be projected for each sweep angle of the detectors. In other words, the linear array of equidistant radioactive point sources may be diagonal to the x-y axis as points must be visible for each sweep angle. It may be further understood that FIG. 21 depicts the linear array of equidistant radioactive point sources as approximately spanning the field of view (FOV) of the detectors. The FOV may be defined as (x0, y0, z0)-(x1, y1, z1), where x0 and x1, y0 and y1, z0 and z1 represent the left, right, lower, upper, outer and inner borders of the FOV, respectively. Furthermore, it may be understood that a distance between points corresponding to the linear array of equidistant radioactive point sources may be such that two or more points will fall on the detector for any detector sweep angle.

Returning to FIG. 20, with the linear array of equidistant radioactive point sources and the Styrofoam object placed roughly parallel to the COR axis, method 2000 proceeds to 2010. At 2010, method 2000 includes performing a scan with several rotation steps each of N degrees. At each rotation step, step 2010 further includes sweeping each detector at an angular step (sweep) of one or degrees for the range pre-determined by the contour of the Styrofoam. Proceeding to 2015, method 2000 includes obtaining a reconstructed image from the data acquired at step 2010. With the reconstructed image obtained at 2015, method 2000 proceeds to 2020. At 2020, method 2000 includes fitting the reconstructed image to an analytical model of the apparatus, where it may be understood that the apparatus comprises the linear array of equidistant radioactive point sources and the Styrofoam object, or in other examples just the linear array of equidistant radioactive point sources.

Proceeding to 2025, method 2000 includes forward projecting the analytical point sources image of step 2020 to generate noise-free projections, and at 2030 method 2000 includes comparing acquired projections to the analytical forward projections. At step 2035, method 2000 includes indicating whether correlation between the acquired projections and the analytical forward projections is within a predetermined tolerance range. If so, method 2000 ends. While method 2000 is depicted as ending, it may be understood that steps 2010 to 2035 may be repeated for each rotation step.

In response to an indication that the correlation between acquired projections and analytical forward projections is not within the predetermined tolerance range, method 2000 proceeds to 2040. At 2040, method 2000 includes applying corrections, for example via applying pitch, yaw, x and y shifts on the plane of detector, to the scan geometry used for the image reconstruction, and then method 2000 returns to 2010 where the process as described is repeated until the correlation between the acquired projections and analytical forward projections are within the predetermined tolerance range. Specifically, offsets of the acquired points from the forward projected analytical points may be used to determine the deviation of the system geometry from that of expected geometry, for applying the corrections.

Thus, briefly, the method of FIG. 20 may be understood to be used for compensating mechanical offsets from ideal system geometry. For example, accurate image reconstruction requires knowledge of the system's geometry. Reconstruction algorithms make assumptions regarding the relationship of the detectors and the object space to simplify the algorithm used for forward and back projection of the images (e.g., Inverse Radon Transformation, rotational reconstruction). For rotational reconstruction algorithms, it is assumed that the y-axis (in an x-y detector space) is parallel to the z-axis of the object space for all views. This enables forward and back projection by simple rotation of the object around the z-axis such that the x and y axes of the detector are parallel to the x and z axes of the object, respectively. Gamma cameras may be flawed by mechanical inaccuracies that can be quantified by calibration procedures. These inaccuracies may be accounted for in the image reconstruction.

Mechanical inaccuracies in which the detector plane is parallel to the xz object plane can be compensated by a 2D translation and rotation of the projection such that the x and y axis of the detector are parallel to the x and z axis of the object, respectively. Alternatively the object may be rotated and translated to achieve the alignment prior to forward and back projection. If the mechanical inaccuracies violate the above (e.g., sagging) additional axes of rotation may be applied to the object, such that the x and y axis of the detector are parallel to the x and z axis of the object respectively, and the relative position of the object to the detector may be preserved prior to forward and back projection.

Thus, discussed here, a method for a nuclear medicine imaging system may comprise acquiring first point source projections of a point source at each of a plurality of detector units over a predetermined number of detector unit rotational steps via a gantry rotor rotation, converting the first point source projections to first center of gravity measurements for each of the plurality of detector units with respect to an x-axis of each of the plurality of detector units, fitting the first center of gravity measurements to obtain a first fit, and obtaining a residual center of gravity determination for each of the plurality of detector units based on a difference between the first center of gravity measurements and the first fit corresponding to each of the plurality of detector units; acquiring second point source projections for each of the plurality of detector units at a predetermined number of sweep angles, converting the second point source projections to second center of gravity measurements for each of the plurality of detector units, fitting the second center of gravity measurements to obtain a second fit for each of the plurality of detector units; and determining a sweep offset for each of the plurality of detector units based on the residual center of gravity determination for each detector unit and the second fit obtained for each detector unit. In a first example of the method, the method may further include wherein the point source is positioned at an arbitrary position in the field of view of each of the plurality of detector units. A second example of the method optionally includes the first example, and further includes wherein the sweep angle for each of the plurality of detector units is fixed for acquiring the first point source projections. A third example of the method optionally includes any one or more or each of the first through second examples, and further comprises correcting a sweep axis zero degree position for each of the plurality of detector units based on the sweep offset determined for each of the plurality of detector units. A fourth example of the method optionally includes any one or more or each of the first through third examples, and further includes wherein the first fit is sinusoidal; and wherein the second fit is linear or approximately linear. A fifth example of the method optionally includes any one or more or each of the first through fourth examples, and further includes wherein the predetermined number of detector unit rotational steps corresponds to each of the plurality of detector units rotating a total of 30 degrees. A sixth example of the method optionally includes any one or more or each of the first through fifth examples, and further includes wherein the predetermined number of detector unit rotational steps is 15, where each detector unit rotational step corresponds to 2 degrees, or where the predetermined number of detector unit rotational steps is 6, where each detector unit rotational step corresponds to 5 degrees. A seventh example of the method optionally includes any one or more or each of the first through sixth examples, and further includes wherein the predetermined number of detector unit rotational steps corresponds to each of the plurality of detector units rotating a total of 60 degrees, where each of the predetermined number of detector unit rotational steps are equally spaced in terms of degree of rotation. An eighth example of the method optionally includes any one or more or each of the first through seventh examples, and further comprises initially acquiring the first point source projections the second point source projections with each of the plurality of detector units at a first radial position with respect to a center of rotation of the nuclear medicine imaging system that is the same for each of the plurality of detector units; and subsequently repeating the acquiring the first point source projections and the second point source projections at a predetermined number of radial positions, determining the sweep offset at each of the predetermined number of radial positions for each of the plurality of detector units, and for each of the plurality of detector units, determining an extrapolated sweep calibration factor based on the sweep offset determined at the predetermined number of radial positions. A ninth example of the method optionally includes any one or more or each of the first through eighth examples, and further comprises excluding one of the plurality of detector units that exhibits a greatest residual center of gravity determination, and re-fitting the first center of gravity measurements to improve the first fit.

Another example of a method for a nuclear medicine imaging system comprises acquiring point source projections of a point source at each of a plurality of detector units over a predetermined number of detector unit rotational steps, converting the point source projections to center of gravity measurements for each of the plurality of detector units with respect to a z-axis of each of the plurality of detector units, determining a median center of gravity determination based on the center of gravity measurements; and determining a residual z-shift offset based on a difference between the center of gravity measurements for each of the plurality of detector units and the median center of gravity determination. In a first example of the method, the method further comprises relying on the residual z-shift offset for each of the plurality of detectors for image reconstruction. A second example of the method optionally includes the first example, and further includes wherein the predetermined number of detector unit rotational steps corresponds to each of the plurality of detector units rotating a total of at least 30 degrees and not more than 60 degrees; and wherein the predetermined number of detector unit rotational steps are equally spaced in terms of degrees. A third example of the method optionally includes any one or more or each of the first through second examples, and further includes wherein the point source is positioned at an arbitrary position within a field of view of each of the plurality of detector units. A fourth example of the method optionally includes any one or more or each of the first through third examples, and further comprises positioning each of the plurality of detector units at a predetermined radial position from a center of rotation of the nuclear medicine imaging system; and wherein the predetermined radial position is the same for each of the plurality of detector units.

An example system comprises a gantry defining a bore, the gantry configured to surround a patient table; a radioactive calibration source positioned at an arbitrary position within the bore; a plurality of detector units coupled to the gantry and configured to detect radiation from the calibration source, each of the plurality of detector units having an x-axis, a y-axis and a z-axis and a sweep axis; and a processor communicatively coupled to the plurality of detector units and configured with instructions in non-transitory memory that when executed cause the controller to: 1) calibrate a sweep axis of each of the plurality of detector units to ensure that at a sweep angle of zero degrees for each of the plurality of detector units, a projection of a center of rotation of the system is aligned with a z-axis of each of the plurality of detector units; 2) calibrate and correct a z-axis of each of the plurality of detector units to ensure that an x-plane and a y-plane of each of the plurality of detector units are aligned and perpendicular to the center of rotation of the system; 3) measure and correct an x-shift of each of the plurality of detector units; and 4) measure and correct a yaw angle of each of the plurality of detector units. In a first example of the system, the system further includes wherein the processor is further configured with instructions in the non-transitory memory that when executed cause the processor to calibrate the sweep axis via a first process that includes: positioning each of the plurality of detectors at a same radial distance from the center of rotation and positioning each of the plurality of detectors at a sweep angle of zero degrees; and acquiring first point source projections of the radioactive calibration source at each of the plurality of detector units over a first predetermined number of detector unit rotational steps, converting the first point source projections to first center of gravity measurements for each of the plurality of detector units with respect to the x-axis, obtain a first fit of the first center of gravity measurements, obtaining a residual center of gravity determination for each of the plurality of detector units based on a difference between the first center of gravity measurements and the first fit corresponding to each of the plurality of detector units; acquiring second point source projections for each of the plurality of detector units at a first predetermined number of sweep angles of each of the plurality of detector units, converting the second point source projections to second center of gravity measurements for each of the plurality of detector units with respect to the x-axis, obtaining a second fit of the second center of gravity measurements for each of the plurality of detector units; determining a sweep offset for each of the plurality of detector units based on the residual center of gravity determination for each of the plurality of detector units and the second fit obtained for each of the plurality of detector units; and correcting a sweep axis zero degree position for each of the plurality of detector units based on the sweep offset determined for each of the plurality of detector units. A second example of the system optionally includes the first example, and further includes wherein the processor is further configured with instructions in the non-transitory memory that when executed cause the processor to calibrate and correct the z-axis of each of the plurality of detector units to ensure that the x-plane and the y-plane of each of the plurality of detector units are aligned and perpendicular to the center of rotation of the system via a second process that includes: positioning each of the plurality of detectors at a same radial distance from the center of rotation and positioning each of the plurality of detectors at a sweep angle of zero degrees; acquiring third point source projections of the radioactive calibration source at each of the plurality of detector units over a second predetermined number of detector unit rotational steps; converting the third point source projections to third center of gravity measurements for each of the plurality of detector units with respect to the z-axis; determining a median center of gravity determination based on the third center of gravity measurements; determining a residual z-shift offset based on a difference between the third center of gravity measurements for each of the plurality of detector units and the median center of gravity determination; and using the z-shift offset for each of the plurality of detector units for image correction. A third example of the system optionally includes any one or more or each of the first through second examples, and further includes wherein the processor is further configured with instructions in the non-transitory memory that when executed cause the processor to measure and correct the x-shift of each of the plurality of detector units via a third process that includes: positioning each of the plurality of detectors at a same radial distance from the center of rotation and positioning each of the plurality of detectors at a sweep angle of zero degrees; acquiring fourth point source projections of the radioactive calibration source at each of the plurality of detector units; converting the fourth point source projections to fourth center of gravity measurements for each of the plurality of detector units with respect to the x-axis; determining an x-shift offset for each of the plurality of detector units based on the fourth center of gravity measurements and source coordinates of the radioactive calibration source; and using the x-shift offset for each of the plurality of detector units for image correction. A fourth example of the system optionally includes any one or more or each of the first through third examples, and further includes wherein the processor is further configured with instructions in the non-transitory memory that when executed cause the processor to measure and correct the yaw angle of each of the plurality of detector units via a fourth process that includes positioning each of the plurality of detectors at a same radial distance from the center of rotation and positioning each of the plurality of detectors at a sweep angle of zero degrees; acquiring fifth point source projections of the radioactive calibration source at each of the plurality of detector units over a predetermined number of positions of the patient table; converting the fifth point source projections to fifth center of gravity measurements for each of the plurality of detector units with respect to the x-axis; determining the yaw angle for each of the plurality of detector units as a function of the fifth center of gravity measurements and the predetermined number of positions of the patient table; and using the yaw angle for each of the plurality of detector units for image correction.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a nuclear medicine imaging system comprising:

acquiring first point source projections of a point source at each of a plurality of detector units over a predetermined number of detector unit rotational steps via a gantry rotor rotation, converting the first point source projections to first center of gravity measurements for each of the plurality of detector units with respect to an x-axis of each of the plurality of detector units, fitting the first center of gravity measurements to obtain a first fit, and obtaining a residual center of gravity determination for each of the plurality of detector units based on a difference between the first center of gravity measurements and the first fit corresponding to each of the plurality of detector units;

acquiring second point source projections for each of the plurality of detector units at a predetermined number of sweep angles, converting the second point source projections to second center of gravity measurements for each of the plurality of detector units, fitting the second center of gravity measurements to obtain a second fit for each of the plurality of detector units; and determining a sweep offset for each of the plurality of detector units based on the residual center of gravity determination for each detector unit and the second fit obtained for each detector unit.

2. The method of claim 1, wherein the point source is positioned at an arbitrary position in the field of view of each of the plurality of detector units.

3. The method of claim 1, wherein the sweep angle for each of the plurality of detector units is fixed for acquiring the first point source projections.

4. The method of claim 1, further comprising correcting a sweep axis zero degree position for each of the plurality of detector units based on the sweep offset determined for each of the plurality of detector units.

5. The method of claim 1, wherein the first fit is sinusoidal; and
wherein the second fit is linear or approximately linear.

6. The method of claim 1, wherein the predetermined number of detector unit rotational steps corresponds to each of the plurality of detector units rotating a total of 30 degrees.

7. The method of claim 6, wherein the predetermined number of detector unit rotational steps is 15, where each detector unit rotational step corresponds to 2 degrees, or where the predetermined number of detector unit rotational steps is 6, where each detector unit rotational step corresponds to 5 degrees.

8. The method of claim 6, wherein the predetermined number of detector unit rotational steps corresponds to each of the plurality of detector units rotating a total of 60 degrees, where each of the predetermined number of detector unit rotational steps are equally spaced in terms of degree of rotation.

9. The method of claim 1, further comprising initially acquiring the first point source projections the second point source projections with each of the plurality of detector units at a first radial position with respect to a center of rotation of the nuclear medicine imaging system that is the same for each of the plurality of detector units; and subsequently repeating the acquiring the first point source projections and the second point source projections at a predetermined number of radial positions, determining the sweep offset at each of the predetermined number of radial positions for each of the plurality of detector units, and for each of the plurality of detector units, determining an extrapolated sweep calibration factor based on the sweep offset determined at the predetermined number of radial positions.

10. The method of claim 1, further comprising excluding one of the plurality of detector units that exhibits a greatest residual center of gravity determination, and re-fitting the first center of gravity measurements to improve the first fit.

11. A method for a nuclear medicine imaging system comprising:

acquiring point source projections of a point source at each of a plurality of detector units over a predetermined number of detector unit rotational steps, converting the point source projections to center of gravity measurements for each of the plurality of detector units with respect to a z-axis of each of the plurality of detector units, determining a median center of gravity determination based on the center of gravity measurements; and determining a residual z-shift offset based on a difference between the center of gravity measurements for each of the plurality of detector units and the median center of gravity determination.

12. The method of claim 11, further comprising relying on the residual z-shift offset for each of the plurality of detectors for image reconstruction.

13. The method of claim 11, wherein the predetermined number of detector unit rotational steps corresponds to each of the plurality of detector units rotating a total of at least 30 degrees and not more than 60 degrees; and wherein the predetermined number of detector unit rotational steps are equally spaced in terms of degrees.

14. The method of claim 11, wherein the point source is positioned at an arbitrary position within a field of view of each of the plurality of detector units.

15. The method of claim 11, further comprising positioning each of the plurality of detector units at a predetermined radial position from a center of rotation of the nuclear medicine imaging system; and wherein the predetermined radial position is the same for each of the plurality of detector units.

16. A system comprising:

a gantry defining a bore, the gantry configured to surround a patient table;

a radioactive calibration source positioned at an arbitrary position within the bore;

a plurality of detector units coupled to the gantry and configured to detect radiation from the calibration source, each of the plurality of detector units having an x-axis, a y-axis and a z-axis and a sweep axis; and a processor communicatively coupled to the plurality of detector units and configured with instructions in non-transitory memory that when executed cause the controller to:

1) calibrate a sweep axis of each of the plurality of detector units to ensure that at a sweep angle of zero degrees for each of the plurality of detector units, a projection of a center of rotation of the system is aligned with a z-axis of each of the plurality of detector units;

2) calibrate and correct a z-axis of each of the plurality of detector units to ensure that an x-plane and a y-plane of each of the plurality of detector units are aligned and perpendicular to the center of rotation of the system;

3) measure and correct an x-shift of each of the plurality of detector units; and 4) measure and correct a yaw angle of each of the plurality of detector units.

17. The system of claim 16, wherein the processor is further configured with instructions in the non-transitory memory that when executed cause the processor to calibrate the sweep axis via a first process that includes:
  positioning each of the plurality of detectors at a same radial distance from the center of rotation and positioning each of the plurality of detectors at a sweep angle of zero degrees; and
  acquiring first point source projections of the radioactive calibration source at each of the plurality of detector units over a first predetermined number of detector unit rotational steps, converting the first point source projections to first center of gravity measurements for each of the plurality of detector units with respect to the x-axis, obtain a first fit of the first center of gravity measurements, obtaining a residual center of gravity determination for each of the plurality of detector units based on a difference between the first center of gravity measurements and the first fit corresponding to each of the plurality of detector units;
  acquiring second point source projections for each of the plurality of detector units at a first predetermined number of sweep angles of each of the plurality of detector units, converting the second point source projections to second center of gravity measurements for each of the plurality of detector units with respect to the x-axis, obtaining a second fit of the second center of gravity measurements for each of the plurality of detector units;
  determining a sweep offset for each of the plurality of detector units based on the residual center of gravity determination for each of the plurality of detector units and the second fit obtained for each of the plurality of detector units; and
  correcting a sweep axis zero degree position for each of the plurality of detector units based on the sweep offset determined for each of the plurality of detector units.

18. The system of claim 16, wherein the processor is further configured with instructions in the non-transitory memory that when executed cause the processor to calibrate and correct the z-axis of each of the plurality of detector units to ensure that the x-plane and the y-plane of each of the plurality of detector units are aligned and perpendicular to the center of rotation of the system via a second process that includes:
  positioning each of the plurality of detectors at a same radial distance from the center of rotation and positioning each of the plurality of detectors at a sweep angle of zero degrees;
  acquiring third point source projections of the radioactive calibration source at each of the plurality of detector units over a second predetermined number of detector unit rotational steps;
  converting the third point source projections to third center of gravity measurements for each of the plurality of detector units with respect to the z-axis;
  determining a median center of gravity determination based on the third center of gravity measurements;
  determining a residual z-shift offset based on a difference between the third center of gravity measurements for each of the plurality of detector units and the median center of gravity determination; and
  using the z-shift offset for each of the plurality of detector units for image correction.

19. The system of claim 16, wherein the processor is further configured with instructions in the non-transitory memory that when executed cause the processor to measure and correct the x-shift of each of the plurality of detector units via a third process that includes:
  positioning each of the plurality of detectors at a same radial distance from the center of rotation and positioning each of the plurality of detectors at a sweep angle of zero degrees;
  acquiring fourth point source projections of the radioactive calibration source at each of the plurality of detector units;
  converting the fourth point source projections to fourth center of gravity measurements for each of the plurality of detector units with respect to the x-axis;
  determining an x-shift offset for each of the plurality of detector units based on the fourth center of gravity measurements and source coordinates of the radioactive calibration source; and
  using the x-shift offset for each of the plurality of detector units for image correction.

20. The system of claim 16, wherein the processor is further configured with instructions in the non-transitory memory that when executed cause the processor to measure and correct the yaw angle of each of the plurality of detector units via a fourth process that includes
  positioning each of the plurality of detectors at a same radial distance from the center of rotation and positioning each of the plurality of detectors at a sweep angle of zero degrees;
  acquiring fifth point source projections of the radioactive calibration source at each of the plurality of detector units over a predetermined number of positions of the patient table;
  converting the fifth point source projections to fifth center of gravity measurements for each of the plurality of detector units with respect to the x-axis;
  determining the yaw angle for each of the plurality of detector units as a function of the fifth center of gravity measurements and the predetermined number of positions of the patient table; and
  using the yaw angle for each of the plurality of detector units for image correction.

* * * * *